US006514938B1

(12) United States Patent
Gad et al.

(10) Patent No.: US 6,514,938 B1
(45) Date of Patent: Feb. 4, 2003

(54) COPOLYMER 1 RELATED POLYPEPTIDES FOR USE AS MOLECULAR WEIGHT MARKERS AND FOR THERAPEUTIC USE

(75) Inventors: Alexander Gad, Nes Ziona (IL); Dora Lis, Hadera (IL)

(73) Assignee: Yeda Research and Development Co. Ltd. at the Weizmann Institute of Science (IL)

( * ) Notice: Subject to any disclaimer, the term of this patent is extended or adjusted under 35 U.S.C. 154(b) by 0 days.

(21) Appl. No.: 09/405,743

(22) Filed: Sep. 24, 1999

Related U.S. Application Data

(60) Provisional application No. 60/101,825, filed on Sep. 25, 1998, and provisional application No. 60/101,693, filed on Sep. 25, 1998.

(51) Int. Cl.[7] .......................... A61K 38/16; C07K 14/00
(52) U.S. Cl. .......................................... 514/12; 530/324
(58) Field of Search ...................... 514/2, 12; 530/350, 530/300, 324

(56) References Cited

U.S. PATENT DOCUMENTS

| | | | |
|---|---|---|---|
| 5,627,206 A | | 5/1997 | Hupe et al. |
| 5,719,296 A | | 2/1998 | Acton, III et al. |
| 5,858,964 A | * | 1/1999 | Aharoni |
| 5,981,589 A | * | 11/1999 | Konfino et al. |

FOREIGN PATENT DOCUMENTS

| | | | |
|---|---|---|---|
| WO | WO9531990 | | 11/1995 |
| WO | WO 95/31990 | * | 11/1995 |

OTHER PUBLICATIONS

Tisch and McDevitt PNAS 91:437–438 (1994).*
Teitelbaum et al (1971) European Journal of Immunology, 1:242–248.*
Teitelbaum et al (1988) PNAS 85(24):9724–9728.*

* cited by examiner

*Primary Examiner*—Patrick J. Nolan
*Assistant Examiner*—Amy DeCloux
(74) *Attorney, Agent, or Firm*—John P. White; Cooper & Dunham LLP

(57) ABSTRACT

The present invention provides molecular weight markers for accurate determination of the molecular weight of glatiramer acetate and other copolymers. The present invention further provides a plurality of molecular weight markers for determining the molecular weight of glatiramer acetate and other copolymers which display linear relationships between molar ellipticity and molecular weight, and between retention time and the log of the molecular weight. The molecular weight markers also optimally demonstrate biological activity similar to glatiramer acetate or corresponding copolymers and can be used for treating or preventing various immune diseases. In addition, the subject invention provides pharmaceutical compositions for the treatment of immune diseases comprising a polypeptide having an identified molecular weight and an amino acid composition corresponding to glatiramer acetate or a terpolymer.

12 Claims, 16 Drawing Sheets

Amino acid from C- Terminus

Amino acid from C- Terminus

Amino acid from C- Terminus

*Amino acid from C- Terminus*

COPOLYMER 1 RELATED POLYPEPTIDES FOR USE AS MOLECULAR WEIGHT MARKERS AND FOR THERAPEUTIC USE

RELATED APPLICATIONS

The present application claims the benefit of U.S. Provisional Application No. 60/101,825, filed Sep. 25, 1998, and U.S. Provisional Application No. 60/101,693, filed Sep. 25, 1998, which are incorporated by reference herein.

INTRODUCTION

The present invention provides molecular weight markers for accurate determination of the molecular weight of glatiramer acetate, terpolymers and other copolymers. The molecular weight markers are polypeptides having identified molecular weights between about 2,000 daltons and about 40,000 daltons, and an amino acid composition corresponding to glatiramer acetate or a related copolymer. Identified molecular weights are provided by polypeptides having defined sequences. Molecular weight markers corresponding to glatiramer acetate comprise the amino acids alanine, glutamic acid, tyrosine and lysine in specific molar ratios. Molecular weight markers corresponding to related terpolymers comprise three of the four amino acids. In a preferred embodiment, the polypeptide has alanine at the N-terminus and tyrosine at the fourth position from the N-terminus. The present invention further provides a plurality of molecular weight markers for determining the molecular weight range of a copolymer composition. The plurality of molecular weight markers ideally displays linear relationships between molar ellipticity and molecular weight, or between retention time and the log of molecular weight.

Optimally, the polypeptides demonstrate biological activity similar to the copolymer from which they are derived. Polypeptides having defined molecular weights and amino acid compositions similar to glatiramer acetate optimally have therapeutic utility for the treatment of immune diseases and conditions.

BACKGROUND OF THE INVENTION

Autoimmune diseases occur when an organism's immune system fails to recognize some of the organism's own tissues as "self" and attacks them as "foreign." Normally, self-tolerance is developed early by developmental events within the immune system that prevent the organism's own T cells and B cells from reacting with the organism's own tissues. These early immune responses are mediated by the binding of antigens to MHC molecules and presentation to T cell receptors.

This self-tolerance process breaks down when autoimmune diseases develop and the organism's own tissues and proteins are recognized as "autoantigens" and attacked by the organism's immune system. For example, multiple sclerosis is believed to be an autoimmune disease occurring when the immune system attacks the myelin sheath, whose function is to insulate and protect nerves. It is a progressive disease characterized by demyelination, followed by neuronal and motor function loss. Rheumatoid arthritis ("RA") is also believed to be an autoimmune disease which involves chronic inflammation of the synovial joints and infiltration by activated T cells, macrophages and plasma cells, leading to a progressive destruction of the articular cartilage. It is the most severe form of joint disease. The nature of the autoantigen(s) attacked in rheumatoid arthritis is poorly understood, although collagen type II is a candidate.

A tendency to develop multiple sclerosis and rheumatoid arthritis is inherited. These diseases occur more frequently in individuals carrying one or more characteristic MHC class II alleles. For example, inherited susceptibility for rheumatoid arthritis is strongly associated with the MHC class II DRB1*0401, DRB 1*0404, or DRB 1*0405 or the DRB1*0101 alleles. The histocompatibility locus antigens (HLA) are found on the surface of cells and help determine the individuality of tissues from different persons. Genes for histocompatibility locus antigens are located in the same region of chromosome 6 as the major histocompatibility complex (MHC). The MHC region expresses a number of distinctive classes of molecules in various cells of the body, the genes being, in order of sequence along the chromosome, the Class I, II and III MHC genes. The Class I genes consist of HLA genes, which are further subdivided into A, B and C subregions. The Class II genes are subdivided into the DR, DQ and DP subregions. The MHC-DR molecules are the best known; these occur on the surfaces of antigen presenting cells such as macrophages, dendritic cells of lymphoid tissue and epidermal cells. The Class III MHC products are expressed in various components of the complement system, as well as in some non-immune related cells.

A number of therapeutic agents have been developed to treat autoimmune diseases, including steroidal and non-steroidal anti-inflammatory drugs, for example, methotrexate; various interferons; and certain inhibitors of prostaglandin synthesis. However, these agents can be toxic when used for more than short periods of time or cause undesirable side effects. Other therapeutic agents bind to and/or inhibit the inflammatory activity of tumor necrosis factor (TNF), for example, anti-TNF specific antibodies or antibody fragments, or a soluble form of the TNF receptor. These agents target a protein on the surface of a T cell and generally prevent interaction with an antigen presenting cell (APC). However, therapeutic compositions containing natural folded proteins are often difficult to produce, formulate, store, and deliver. Moreover, the innate heterogeneity of the immune system can limit the effectiveness of drugs and complicate long-term treatment of autoimmune diseases.

Glatiramer acetate (Copolymer 1; Cop 1; hereinafter GLAT copolymer) is a mixture of polypeptides composed of alanine, glutamic acid, lysine, and tyrosine in a molar ratio of approximately 4.6:1.5:3.6:1.0, respectively, which is synthesized by chemically polymerizing the four amino acids, forming products with average molecular weights ranging from about 4000 to about 13,000 daltons. The corresponding molar fractions are approximately 0.427 for alanine, 0.141 for glutamic acid, 0.337 for lysine and 0.093 for tyrosine, and may vary by about +/–10%. Related copolymers are mixtures of polypeptides composed of three (thus, "terpolymers") of the four aforementioned amino acids. Copolymer 1 and the terpolymers address the innate heterogeneity of the mammalian immune system and human population and are effective for treatment of autoimmune diseases and other immune conditions. Preferred average molecular weight ranges and processes of making terpolymers are described in U.S. Pat. No. 5,800,808, which is hereby incorporated by reference in its entirety. Also contemplated by the invention are other copolymers comprised of other combinations of three, four, or five or more amino acids.

To certify a Copolymer 1 or terpolymer preparation for use in a pharmaceutical products, it is necessary to accurately determine the molecular weight distribution of the polypeptides in the preparation. One method for determining the molecular weight is chromatography on a Superose 12 column. Calibration coefficients of columns for determination of glatiramer acetate molecular weight have been determined using glatiramer acetate batches with indirectly measured molecular weights. Indirect measures have included viscosimetry and velocity-sedimentation ultracentrifugation. More recently, batches of glatiramer acetate markers have been prepared whose molecular weights were determined by multiple angle laser light scattering (MALLS).

Thus, a need exists for molecular weight markers useful as standards for determining the molecular weight distribution of copolymer compositions contemplated by the invention. Desirable molecular weight markers have defined molecular weights and physical properties which are analogous to the molecules for which molecular weight is to be determined. Ideally, there is a linear relationship between the defined molecular weights (or the log of the defined molecular weights) of the markers and a measurable physical property such as, for example, the molar ellipticity of the markers, or the retention time of the markers on a molecular sizing column.

SUMMARY OF THE INVENTION

Sequence-defined molecular weight markers that have chemical and physical characteristics similar to GLAT copolymer provide an accurate and robust calibration set for determinations of molecular weight of production batches. The present invention provides derivatives of GLAT copolymer useful as molecular weight markers for determining the molecular weight ranges of GLAT copolymer preparations and optimally having therapeutic utility for treatment of immune conditions. The invention further provides polypeptides having defined molecular weights which are derivatives of other copolymers and which are useful for determining molecular weight ranges of preparations of those copolymers. When those copolymers are therapeutically useful, the derivative polypeptides optimally have therapeutic utility. For determination of the molecular weight range of a GLAT copolymer preparation, the preferred derivative is a polypeptide having an amino acid composition corresponding approximately to GLAT copolymer and an identified molecular weight which is between about 2,000 daltons and about 40,000 daltons. The polypeptide preferably has specific molar ratios of amino acids alanine, glutamic acid, tyrosine and lysine. Moreover, in a preferred embodiment the polypeptide has alanine at the N-terminus and tyrosine at the fourth position from the N-terminus. For determination of the molecular weight of a terpolymer, the preferred derivative will have a defined molecular weight and an amino acid composition corresponding approximately to that of the terpolymer. Other copolymers are also contemplated by the invention. When determining of the molecular weight of a copolymer contemplated by the invention, the polypeptide derivative will have a defined molecular weight and an amino acid composition corresponding approximately to that of the copolymer.

The present invention further provides a plurality of molecular weight markers for determining the molecular weight of glatiramer acetate or a terpolymer or other copolymer on a molecular weight sizing column. The markers comprise two to ten or more polypeptides, each polypeptide having an identified molecular weight. When determining the molecular weight range of glatiramer acetate, a preferred plurality of molecular weight markers will have defined molecular weights from about 2,000 daltons to about 40,000 daltons, and amino acid compositions corresponding to glatiramer acetate or a selected terpolymer. In preferred embodiments, there is a linear relationship between the log molecular weight of the polypeptide molecular weight markers and either the retention time of the molecular weight markers on a sizing column or between the molecular weight of the molecular weight markers and the molar ellipticity of the molecular weight markers.

The present invention further provides pharmaceutical compositions which include a therapeutically effective amount of a polypeptide useful as a molecular weight marker for determining the molecular weight range of GLAT copolymer and consisting essentially of amino acids alanine, glutamic acid, tyrosine and lysine in molar fractions of from about 0.38 to about 0.50 alanine, from about 0.13 to about 0.15 glutamic acid, from about 0.08 to about 0.10 tyrosine, and from about 0.3 to about 0.4 lysine, and a pharmaceutically acceptable carrier.

The present invention further provides pharmaceutical compositions which include a therapeutically effective amount of a polypeptide useful as a molecular weight marker for determining the molecular weight range of a terpolymer and consisting essentially of amino acids alanine, tyrosine, and lysine in the molar fractions of from about 0.3 to about 0.6 alanine, from about 0.005 to about 0.25 tyrosine, and from about 0.1 to about 0.5 lysine, and a pharmaceutically acceptable carrier. The polypeptide is preferably substantially free of glutamic acid.

The present invention further provides pharmaceutical compositions which include a therapeutically effective amount of a polypeptide useful as a molecular weight marker for determining the molecular weight range of a terpolymer and consisting essentially of glutamic acid, tyrosine and lysine in molar fractions of from about 0.005 to about 0.300 glutamic acid, from about 0.005 to about 0.250 tyrosine, and from about 0.3 to about 0.7 lysine, and a pharmaceutically acceptable carrier. The polypeptide is preferably substantially free of alanine.

The present invention further provides pharmaceutical compositions which include a therapeutically effective amount of a polypeptide useful as a molecular weight marker for determining the molecular weight range of a terpolymer and consisting essentially of amino acids alanine, glutamic acid and tyrosine in molar fractions of from about 0.005 to about 0.8 alanine, from about 0.005 to about 0.3 glutamic acid, and from about 0.005 to about 0.25 tyrosine, and a pharmaceutically acceptable carrier. The polypeptide is preferably substantially free of lysine.

The present invention also provides pharmaceutical compositions which includes a therapeutically effective amount of a polypeptide useful as a molecular weight marker for determining the molecular weight range of a terpolymer and consisting essentially of alanine, glutamic acid and lysine, in molar fractions of from about 0.005 to about 0.6 alanine, from about 0.005 to about 0.3 glutamic acid, and from about 0.2 to about 0.7 lysine, and a pharmaceutically acceptable carrier. The polypeptide is preferably substantially free of tyrosine.

In general, pharmaceutical compositions of the invention include therapeutically effective amounts of a polypeptide which is useful as a molecular weight marker for determining the molecular weight range of a copolymer of any number (e.g., three to five or more) of amino acids. In the manner of glatiramer acetate, such a copolymer is a diverse population of sequences of the amino acids. The polypeptide useful as a molecular weight marker consists of those amino acids in molar fractions corresponding approximately to the copolymer.

The present invention further provides methods for treating and preventing immune-mediated and autoimmune diseases in a mammal which include administering a therapeutically effective amount of a molecular weight marker of the invention. In another embodiment, the method for treating immune-mediated and autoimmune diseases in a mammal further involves inhibiting proliferation of T cells involved in the immune attack. In another embodiment, the method for treating immune-mediated and autoimmune diseases in a mammal involves binding a molecular weight marker of the invention to an antigen presenting cell. In yet another embodiment, the method for treating immune-mediated and autoimmune disease in a mammal involves binding a molecular weight marker of the invention to a major histocompatibility complex class II protein which is associated with autoimmune diseases.

Autoimmune diseases contemplated by the present invention include arthritic conditions, demyelinating diseases and inflammatory diseases. For example, autoimmune diseases which can be treated by the present compositions include multiple sclerosis, rheumatoid arthritis, osteoarthritis, autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Graves disease, Guillain-Barre's syndrome, Hashimoto's disease, idiopathic myxedema, myasthenia gravis, psoriasis, pemphigus vulgaris, or systemic lupus erythematosus.

Immune-mediated diseases result from undesired sensitivity of the immune system to particular foreign antigens. Examples are host-versus-graft disease (HVGD) and graft-versus-host disease (GVHD) and numerous types of delayed-type hypersensitivity (DTH).

The present compositions can be used to treat one or more of these diseases.

BRIEF DESCRIPTION OF THE DRAWINGS

FIGS. 1b-1, 1b-2 and 1b-3 provide the distribution of lysine in the TV-markers described in Table 1. The amino acid position is defined by the X-axis. The presence of a lysine residue is indicated by a vertical bar at the indicated amino acid position.

FIGS. 1c-1, 1c-2 and 1c-3 provide the distribution of glutamic acid in the TV-markers described in Table 1. The amino acid position is defined by the X-axis. The presence of a glutamic acid residue is indicated by a vertical bar at the indicated amino acid position.

FIGS. 1d-1, 1d-2 and 1d-3 provide the distribution of tyrosine in the TV-markers described in Table 1. The amino acid position is defined by the X-axis. The presence of a tyrosine residue is indicated by a vertical bar at the indicated amino acid position.

FIG. 2 provides a plot of the molar ellipticity versus molecular weight of the present TV-markers compared to known glatiramer acetate markers. The molar ellipticity is provided in $10^{-5}$ deg $cm^{-2}$ $dmole^{-1}$ and the molecular weight is in daltons. Circles indicate TV-markers and squares depict glatiramer acetate markers. As shown, the TV-markers provide a linear relationship between molar ellipticity and molecular weight.

DETAILED DESCRIPTION OF THE INVENTION

Figures 1, 1A:
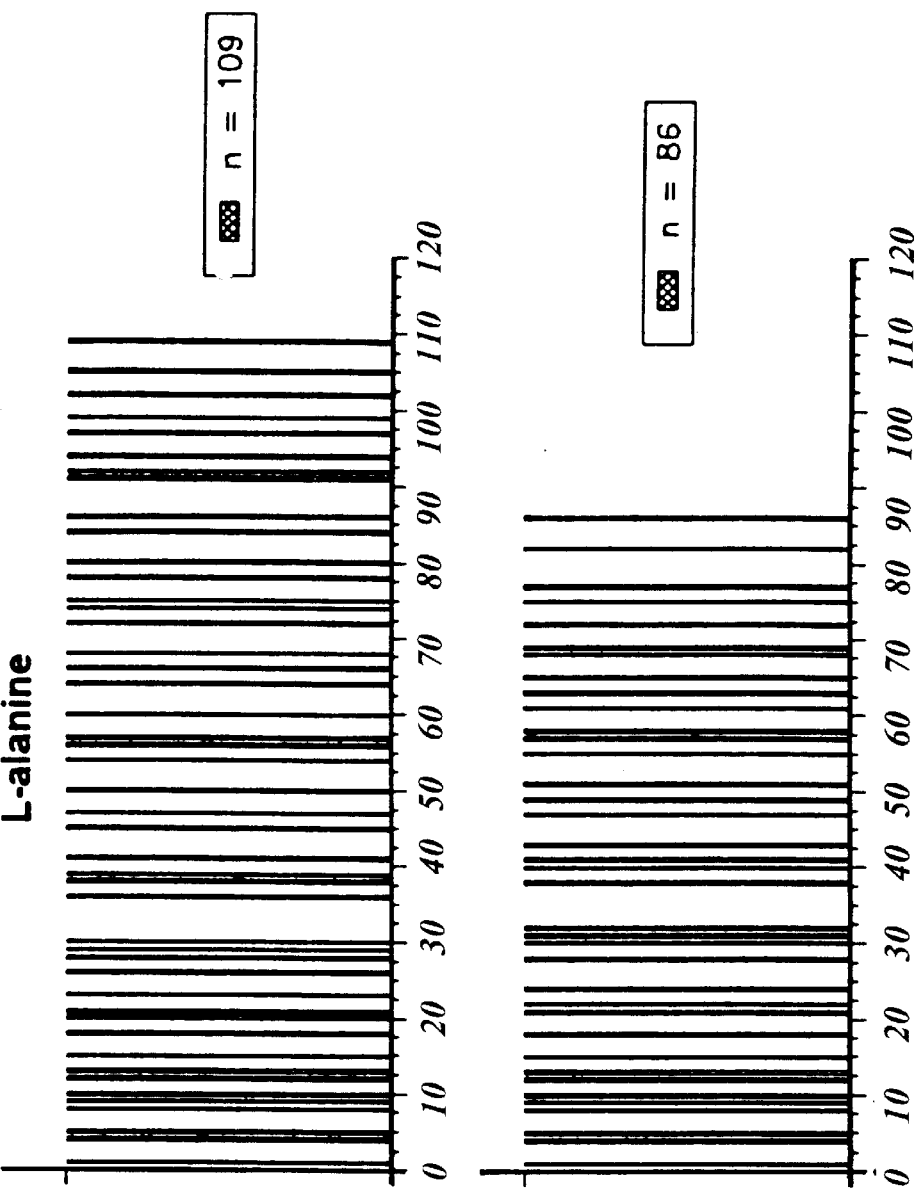
FIGS. 1a-1, 1a-2 and 1a-3 provide the distribution of alanine in the molecular markers (TV-markers) described in Table 1. The amino acid position is defined by the X-axis. The presence of an alanine is indicated by a vertical bar at the indicated amino acid position.

Molecular weight markers of the invention (e.g., TV-markers), include polypeptides having an amino acid composition approximately corresponding to glatiramer acetate or related terpolymers, and an identified molecular weight which is between about 2,000 daltons and about 40,000 daltons and are useful for accurately determining the molecular weight of GLAT copolymer and related terpolymers. It follows from the requirement for an identified molecular weight that a TV-marker should have a discrete molecular weight and not a range of molecular weights. Accordingly, TV-markers are synthesized according to a predetermined amino acid sequence which corresponds in composition to the copolymer for which molecular weight range is to be determined. Optimally, TV-markers have therapeutic activity which is similar to corresponding copolymer. These markers can be used in any molecular size discrimination system using any available molecular weight determination procedure or apparatus. For example, the present markers can be used for calibration of any chromatographic procedure or apparatus which is used for molecular weight determinations of polypeptides or proteins. Such a chromatographic apparatus can be a molecular weight sizing column which separates polypeptides on the basis of their molecular size. Examples of molecular weight sizing columns include TSK columns, Sephadex columns, Sepharose columns, and Superose columns. In order to provide molecular weight markers of discrete size and composition, molecular weight markers of the invention can be synthesized according to predetermined sequences by methods which are well known to those of skill in the art.

Amino acids of the present invention include, but are not limited to the 20 commonly occurring amino acids. Also included are naturally occurring and synthetic derivatives, for example, selenocysteine. Amino acids further include amino acid analogues. An amino acid "analogue" is a chemically related form of the amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a peptide or polypeptide.

The phrases "amino acid" and "amino acid sequence" as defined here and in the claims can include one or more components which are amino acid derivatives and/or amino acid analogs comprising part or the entirety of the residues for any one or more of the 20 naturally occurring amino acids indicated by that sequence. For example, in an amino acid sequence having one or more tyrosine residues, a portion of one or more of those residues can be substituted with homotyrosine. Further, an amino acid sequence having one or more non-peptide or peptidomimetic bonds between two adjacent residues, is included within this definition.

The one letter and three letter amino acid codes (and the amino acid that each represents) are as follows: A means ala (alanine); C means cys (cysteine); D means asp (aspartic acid); E means glu (glutamic acid); F means phe (phenylalanine); G means gly (glycine); H means his (histidine); I means ile (isoleucine); K means lys (lysine); L means leu (leucine); M means met (methionine); N means asn (asparagine); P means pro (proline); Q means gln (glutamine); R means arg (arginine); S means ser (serine); T means thr (threonine); V means val (valine); W means trp (tryptophan); and Y means tyr (tyrosine).

The term "hydrophobic" amino acid is defined here and in the claims as including aliphatic amino acids alanine (A, or ala), glycine (G, or gly), isoleucine (I, or ile), leucine (L, or leu), proline (P, or pro), and valine (V, or val), the terms in parentheses being the one letter and three letter standard code abbreviation s for each amino acid, and aromatic amino acids tryptophan (W, or trp), phenylalanine (F or phe), and tyrosine (Y, or tyr). The amino acids confer hydrophobicity as a function of the length of aliphatic and size of aromatic side chains, when found as residues within a protein.

The term "charged" amino acid is defined here and in the claims as including an amino acids aspartic acid (D, or asp), glutamic acid (E, or glu), histidine (H, or his), arginine (R, or arg) and lysine (K, or lys), which confer a positive (his, lys and arg) or negative (asp and gly) charge at physiological values of pH in aqueous solutions on proteins containing these residues.

Polypeptide Compositions Contemplated by the Invention—According to the present invention, polypeptides having defined molecular weights a or all four of the amino acids tyrosine, glutamic acid, alanine and lysine are preferred for the present markers. However, one of skill in the art can readily substitute structurally-related amino acids without deviating from the spirit of the invention. Thus, the present invention further contemplates conservative amino acid substitutions for tyrosine, glutamic acid, alanine and lysine in the present polypeptides. Such structurally-related amino acids include those amino acids which have about the same charge, hydrophobicity and size as tyrosine, glutamic acid, alanine or lysine. For example, lysine is structurally-related to arginine and histidine; glutamic acid is structurally-related to aspartic acid; tyrosine is structurally-related to serine, threonine, tryptophan and phenylalanine; and alanine is structurally-related to valine, leucine and isoleucine.

Moreover, molecular weight markers of the invention can be composed of L- or D-amino acids. As is known by one of skill in the art, L-amino acids occur in most natural proteins. However, D-amino acids are commercially available and can be substituted for some or all of the amino acids used to make molecular weight markers of the invention. The present invention contemplates molecular weight markers formed from mixtures of D- and L-amino acids, as well as molecular weight markers consisting essentially of either L- or D-amino acids.

The average molecular weight and the average molar fraction of the amino acids in the present polypeptides can vary. However, a molecular weight range of about 2,000 to about 40,000 is contemplated, and basic polypeptides, rather than acidic polypeptides, are preferred.

In one embodiment, the present invention provides polypeptide markers containing tyrosine, alanine, glutamic acid and lysine in defined molar ratios. In a more preferred embodiment, the molar ratio of amino acids of the present polypeptides is that found in GLAT copolymer. Such a correspondence in molar ratios provides the best molecular weight markers because those markers will have a charge and a molecular shape which is similar to that of GLAT copolymer. When structurally dissimilar markers are used, the markers may migrate or elute somewhat differently from GLAT copolymer preparations, even though those preparations have the same molecular weight as the markers.

Moreover, in a preferred embodiment, alanine is at the N-terminus and tyrosine is at position four from the N-terminus. Edman degradation analyses performed on various glatiramer acetate batches revealed a greater abundance of alanine at the N-terminus and tyrosine at position four from the N-terminus. Therefore, in certain preferred embodiments, GLAT copolymer molecular weight markers have alanine at the N-terminus and tyrosine at position four from the N-terminus. Studies of the polymerization reaction used to synthesize GLAT copolymer have indicated that alanine and glutamic acid polymerize faster than lysine. As a result, the C-terminal portion of GLAT copolymer tends to be richer in alanine and glutamic acid, whereas the N-terminal portion tends to be richer in lysine. In preferred embodiments, the distribution of amino acid residues in GLAT copolymer molecular weight markers reflects this bias.

When determining the molecular weight range of GLAT copolymer, a preferred molecular weight marker consists essentially of amino acids alanine, glutamic acid, tyrosine and lysine in molar fractions of from about 0.38 to about 0.50 alanine, from about 0.13 to about 0.15 glutamic acid, from about 0.08 to about 0.10 tyrosine, and from about 0.3 to about 0.4 lysine.

In other embodiments, the present invention provides molecular weight markers containing three of the four amino acids alanine, glutamic acid, tyrosine, and lysine in defined ratios. In preferred embodiments, the molar fractions of amino acids present the molecular weight markers correspond to that found in a corresponding terpolymer.

When the molecular weight marker contains alanine, glutamic acid and tyrosine, alanine can be present in a mole fraction of about 0.005 to about 0.800, glutamic acid can be present in a mole fraction of about 0.005 to about 0.300, and tyrosine can be present in a mole fraction of about 0.005 to about 0.250. The molecular weight is from about 2,000 to about 40,000 daltons, and preferably from about 3000 to about 12,000 daltons.

When the molecular weight marker contains alanine, glutamic acid and lysine, alanine can be present in a mole fraction of about 0.005 to about 0.600, glutamic acid can be present in a mole fraction of about 0.005 to about 0.300, and lysine can be present in a mole fraction of about 0.2 to about 0.7. The molecular weight is between about 2,000 and about 40,000 daltons, and preferably between about 3000 and about 12,000 daltons.

When the molecular weight marker contains alanine, tyrosine and lysine, alanine can be present in a mole fraction of about 0.3 to about 0.6, tyrosine can be present in a mole fraction of about 0.005 to about 0.250, and lysine can be present in a mole fraction of about 0.1 to about 0.5. The molecular weight is between about 2,000 and about 40,000 daltons, and preferably between about 3000 and about 12,000 daltons.

When the molecular weight marker contains glutamic acid, tyrosine and lysine, glutamic acid can be present in a mole fraction of about 0.005 to about 0.300, tyrosine can be present in a mole fraction of about 0.005 to about 0.250, and lysine can be present in a mole fraction of about 0.3 to about 0.7. The molecular weight is between about 2,000 and about 40,000 daltons, and preferably between about 3000 and about 12,000 daltons.

Polypeptides of the invention can be used for molecular weight range determinations of other copolymers contemplated by the invention. Contemplated copolymers can consist of combinations of three, four, or five or more amino acids. In general, in order to determine the molecular weight range of a copolymer contemplated by the invention, the polypeptide molecular weight marker will have a defined molecular weight and an amino acid composition corresponding approximately to that of the copolymer. It will be apparent to one of skill in the art that any bias in the distribution of amino acids in a copolymer can be determined as described above for GLAT copolymer. For example, the relative amounts of amino acids incorporated at each position of a terpolymer population can be obtained by analyzing the products of each step of an Edman degradation. Alternatively, the proportions of amino acids incorporated into a terpolymer population during synthesis can be monitored. Where applicable, molecular weight markers can then be synthesized which reflect the bias. In addition, certain preferred terpolymer molecular weight markers will have alanine or tyrosine at position four.

Examples of preferred polypeptide molecular weight marker sequences are given in Table 1 (SEQ ID NOS: 1–7) using the conventional single letter amino acid code and reading from N-terminal to C-terminal. The seven indicated sequences are individual preparations of polypeptides having an amino acid composition corresponding to glatiramer acetate. Usually, amino acids comprising a molecular weight marker molecule are predominantly of one configuration (D- or L-configuration). In preferred embodiments, a molecular weight marker molecule is composed entirely of amino acids of the same configuration. However, molecular weight marker molecules comprising amino acids of mixed configuration may be preferred in certain embodiments where molecular weight is being determined for a glatiramer acetate preparation comprising amino acids of mixed configuration.

TABLE 1

Selected TV-markers amino acid sequences

| TV-## | SEQ ID NO | Sequence |
| --- | --- | --- |
| TV-35 | 1 | AKKYAKKEKAAKKAYKKEAKAKAAEAAAKEAAYEA |
| TV-45 | 2 | AKKYAKKAKAEKAKKAYKAAEAKKAAKYEKAAAEKAAAKE-AAYEA |
| TV-56 | 3 | AKKYAKKEKAYAKKAEKAAKKAEAKAYKAAEAKKKAEAKY-KAEAAKAAAKEAAYEA |
| TV-66 | 4 | AKKYAKKEKAYAKAKKAEAKAAKKAKAEAKKYAKAAKAEK-KEYAAAEAKYKAEAAKAAAKEAAYEA |
| TV-77 | 5 | AKKYAKKEKAYAKKAEKAAKKAEAKAYKAAEAKKKAKAEA-KKYAKAAKAEKKEYAAAEAKYKAEAAKAAAKEAAYEA |
| TV-86 | 6 | AKKYAKKEKAYAKKAEKAAKKAEAKAYKAAEAKKKAKAEA-KKYAKAAKAEKKEYAAAEAKYKAEAAKKAYKAEAAKAAAK-EAAYEA |

TABLE 1-continued

Selected TV-markers amino acid sequences

| TV-## | SEQ ID NO | Sequence |
| --- | --- | --- |
| TV-109 | 7 | AKKYAKKAEKAYAKKAKAAKEKKAYAKKEAKAYKAAEAKK-KAKAEAKKYAKEAAKAKKEAYKAEAKKYAKAAKAEKKEYA-AAEAKKAEAAKAYKAEAAKAAAKEAAYEA |

In another embodiment, the present invention provides a plurality of molecular weight markers for determining the molecular weight of glatiramer acetate or a terpolymer on a molecular weight sizing column. The plurality of molecular weight markers are polypeptides. The plurality of markers can be two to about ten or more. In a preferred embodiment, the plurality of markers is about seven. Each polypeptide has an identified molecular weight which is between about 2,000 daltons and about 40,000 daltons, and an amino acid composition which corresponds approximately to that of glatiramer acetate or a terpolymer.

When such a plurality of molecular weight markers are used as standards for determining the molecular weight of glatiramer acetate or a terpolymer, a relationship which is approximately linear exists between the retention time of the molecular weight markers on the chromatographic column and the log of the molecular weight. A plurality of markers is used which is sufficient to establish the approximately linear relationship, although more may be employed. FIG. 3 shows the approximately linear relationship between relative retention time and log molecular weight for TV-markers of the invention.

In another embodiment, an approximately linear relationship exists between the molar ellipticity of the molecular weight markers and the molecular weight of the markers. When determining the molecular weight of a glatiramer acetate preparation by molar ellipticity, a plurality of markers is used which is sufficient to establish the approximately linear relationship, although more may be employed. A molecular weight for the glatiramer acetate or terpolymer preparation is then obtained based on the linear relationship. FIG. 2 shows the approximately linear relationship between molar ellipticity and molecular weight for TV-markers of the invention.

Pharmaceutical Compositions Contemplated by the Invention—Molecular weight markers of the invention which correspond in composition to GLAT copolymer optimally have biological activity, and can be used for treatment of disease in the manner of GLAT copolymer. TV-markers having biological activity are alternately referred to as therapeutic markers. For example, GLAT copolymer is useful for the treatment of MS in humans as well as for blocking experimental allergic encephalomyelitis (EAE) in mice. Polypeptides of the invention having identified molecular weights and amino acid compositions corresponding to GLAT copolymer are shown herein to be active in the mouse model as well and demonstrate immunological characteristics which are similar to those of GLAT copolymer. Monoclonal antibodies which bind to GLAT copolymer also bind to TV-markers. Additionally, certain T cells which are stimulated by GLAT copolymer are also stimulated by molecular weight markers of the invention.

Similarly, a polypeptide having a defined molecular weight and corresponding in amino acid composition to a terpolymer having therapeutic utility will optimally have therapeutic utility. In general, polypeptide molecular weight markers corresponding in composition to a biologically active copolymer will optimally have similar biological activity.

The present molecular weight markers can be formulated into pharmaceutical compositions containing a pharmaceutically acceptable carrier. As used herein, "pharmaceutically acceptable carrier" includes any and all solvents, dispersion media, coatings, antibacterial and antifungal agents, isotonic and absorption delaying agents, sweeteners and the like. The pharmaceutically acceptable carriers may be prepared from a wide range of materials including, but not limited to, flavoring agents, sweetening agents and miscellaneous materials such as buffers and absorbents that may be needed in order to prepare a particular therapeutic composition. The use of such media and agents with pharmaceutically active substances is well known in the art. Except insofar as any conventional media or agent is incompatible with the active ingredient, its use in the therapeutic compositions is contemplated. Supplementary active ingredients can also be incorporated into the compositions. The present compositions may be formulated as an injectable solution or suspension, a spray solution or a suspension.

Pharmaceutical compositions comprise an amount of one or more molecular weight markers of the invention. Preferably, the molecular weight markers consist essentially of three or all four of the amino acids tyrosine, alanine, glutamic acid and lysine in defined molar fractions. The molar fractions of the amino acids will be as set forth above.

In one embodiment, the molecular weight markers of the pharmaceutical composition are capable of binding to an MHC class II protein which, preferably, is associated with an autoimmune disease. The Class II MHC protein consists of approximately equal-sized α and β subunits, both of which are transmembrane proteins. A peptide-binding cleft is formed by parts of the amino termini of both α and β subunits. This peptide-binding cleft is the sit of presentation of the antigen to T cells There are at least three types of Class II MHC molecules: HLA-DR, HLA-DQ, and HLA-DP molecules. There are also numerous alleles encoding each type of these HLA molecules. The Class II MHC molecules are expressed predominantly on the surfaces of B lymphocytes and antigen presenting cells such as macrophages. Any available method can be used to ascertain whether the molecular weight marker binds to one or more MHC class II proteins. For example, the polypeptide can be radiolabeled or biotinylated, mixed with a crude or pure preparation of MHC class II protein and binding detected by adherence of the reporter molecule to the MHC class II protein after removal of the unbound polypeptide.

In another embodiment, the molecular weight markers are capable of binding to an MHC class II protein associated with multiple sclerosis. A polypeptide of this embodiment can have similar or greater affinity for the antigen binding groove of an MHC class II protein associated with multiple sclerosis than does Copolymer 1. Hence, the contemplated polypeptide can inhibit binding of or displace the binding of myelin autoantigens from the MHC class II protein. One MHC class II protein associated with multiple sclerosis is HLA-DR4 (DRB1*1501).

In another embodiment, molecular weight markers of the invention are capable of binding to an MHC class II protein associated with an arthritic condition, for example, rheumatoid arthritis or osteoarthritis. Accordingly, a polypeptide of this embodiment can have a greater affinity for the antigen binding groove of an MHC class II protein associated with the autoimmune disease than does a type type II collagen 261–273 peptide. Hence, the contemplated polypeptide can inhibit binding of, or displace the type type II collagen 261–273 peptide from the antigen binding groove of an MHC class II protein.

Therapeutic Methods Contemplated by the Invention—The present invention further provides methods for treating and preventing immune diseases in a mammal which include administering a therapeutically effective amount of a composition comprising a molecular weight marker of the invention.

Autoimmune diseases contemplated by the present invention include either cell-mediated disease (e.g. T cell) or antibody-mediated (e.g. B cell) disorders. Such disorders can be, interalia, arthritic conditions, demyelinating diseases and inflammatory diseases. For example, autoimmune diseases which can be treated by the present polypeptides include multiple sclerosis (MS), rheumatoid arthritis (RA), osteoarthritis, autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Graves disease, Guillain-Barre's syndrome, Hashimoto's disease, idiopathic myxedema, myasthenia gravis, psoriasis, pemphigus vulgaris, or systemic lupus erythematosus, The present compositions can be used to treat one or more of these diseases.

The term "arthritic condition" as used herein is a condition wherein at least one symptom of rheumatoid arthritis is observed in at least one joint of a mammal, for example in a shoulder, knee, hip, backbone or a digit of the mammal. Examples of arthritic conditions include "polyarthritis", which is an arthritic condition that affects more than a single joint; "juvenile arthritis", an arthritic condition of humans under the age of 21; and Felty's syndrome, which can include the symptoms of neutropenia, splenomegaly, weight loss, anemia, lymphadenopathy, and pigment spots on the skin.

Immune-mediated diseases contemplated by the present invention are characterized by undesirable immune hypersensitivity to one or more antigens and include host-versus-graft disease (HVGD) and graft-versus-host disease (GVHD), which are exemplified, respectively, by graft rejection by the host immune system and by attack on the host by donor T cells. These diseases are a significant barrier to transplantation systems such as organ transplantations and bone marrow reconstitutions. Other contemplated immune mediated diseases include delayed-type hypersensitivity (DTH) which is associated with contact antigens such as poison ivy and poison oak and various chemicals, as well as tuberculosis, leprosy, leishmaniasis, deep fungal infections, etc.

In one embodiment, any autoimmune disease can be treated by the present molecular weight markers so long as the contemplated marker binds to an MHC class II protein that has been associated with the autoimmune disease. One aspect of this embodiment provides a method which includes selecting a molecular weight marker that inhibits binding of an antigenic peptide to an MHC class II protein, for example, a method which further comprises selecting the molecular weight marker that inhibits class II-specific T cell responses to an MHC class II protein-peptide complex, and a method wherein the antigenic peptide is associated with an autoimmune disease; in another embodiment of the invention, a method is provided wherein the MHC class II protein is associated with an autoimmune disease.

In another embodiment, the method for treating an autoimmune disease in a mammal further involves inhibiting the proliferation or function of T cells which are responsive to an autoantigen. RA is a T cell-mediated autoimmune disease which can be treated with the present polypeptides. The pathological process of autoimmune diseases and immune rejection is mediated by T cells. Upon binding to and recognition of an antigen, T cells proliferate, secrete cytokines and recruit additional inflammatory and cytotoxic cells to the site. The present molecular weight markers prevent T cell proliferation and T cell functions such as cytokine secretion and recruitment of inflammatory and cytotoxic cells to the site. When the autoimmune disease is an arthritic condition the autoantigen can be collagen, and the present molecular weight markers can inhibit the proliferation and function of collagen-responsive T cells.

In another embodiment, the method for treating an autoimmune disease in a mammal involves binding the molecular weight marker to an antigen presenting cell such as a macrophage, a dendritic cell of the lymphoid tissue or an epidermal cell. The proliferation and functions of a T cell are activated when an appropriate antigen is presented to it. By binding to antigen presenting cells, the present molecular weight markers may block or otherwise interfere with T cell activation.

In yet another embodiment, the method for treating an autoimmune disease in a mammal involves binding the molecular weight marker to a major histocompatibility complex class II protein which is associated with an autoimmune disease. The Class II MHC proteins are expressed predominantly on the surfaces of B lymphocytes and antigen presenting cells such as macrophages. These Class II MHC proteins have a peptide-binding cleft which is the site at which antigenic peptides are presented to T cells. When the present polypeptides bind to a major histocompatibility complex class II protein, those polypeptides can block or otherwise interfere with antigen presentation and/or T cell activation.

In another embodiment, the method for treating an autoimmune disease in a mammal involves binding the molecular weight marker to Copolymer 1-reactive B cell antibodies, and/or Copolymer 1-reactive T cells. Copolymer 1-reactive $T_H 2/3$ T cells facilitate the therapeutic effects of Copolymer 1. When binding to Copolymer 1-reactive T cells, the present molecular weight markers stimulate those T cells proliferate, secrete antiinflammatory cytokines and enhance the therapeutic benefits of treatment by the present methods. According to the present invention, the present molecular weight markers also bind to autoantigen-reactive antibodies which may block the antibody from attacking the target tissue, thereby helping to prevent the autoimmune disease from progressing.

The present molecular weight markers may be administered by any convenient route. In one embodiment the present molecular weight markers can be administered by injection to facilitate delivery to the tissues affected by the autoimmune disease. Thus, the present molecular weight markers may, for example, be injected, ingested, inhaled, or topically applied. The subject molecular weight markers may be incorporated into a cream, solution or suspension for topical administration. The present molecular weight markers are preferably administered orally, topically or by injection without addition of an adjuvant.

Useful Kits of the Invention—In an embodiment of the invention, a kit is provided for assaying the binding of an analyte to an MHC protein, which includes a water-soluble MHC protein, for example which has been recombinantly produced in a non-mammalian cell, and a means for detection of the bound analyte on the MHC protein, and instructions for use. The MHC protein used in the kit is an MHC class II protein selected from the group consisting of an MHC class II HLA-DR1 protein, an MHC class II HLA-DR2 protein and an MHC class II HLA-DR4 protein. The kit can further comprise an autoantigenic peptide. A kit of the invention can be used, for example, to test binding of a molecular weight marker of the invention to an MHC class II or inhibition of MHC binding of an autoantigenic peptide.

In a preferred embodiment, the MHC class II protein is produced in an invertebrate or a microbial cell, such as an insect cell or a yeast cell and is therefore devoid of bound peptide in the antigen cleft. The means for detecting binding of the analyte to the MHC protein can be any radioactive, fluorimetric, chemiluminescent, enzymatic or colorimetric means known to one of ordinary skill in the art. In a preferred embodiment, the MHC protein is a class II HLA-DR1 or HLA-DR4 protein. Examples of preferred autoantigenic peptide to be included are a collagen type II peptide, a peptide derived from myelin basic protein, myelin oligodendrite protein, or a peptide from another protein implicated in an autoimmune disease.

The examples which follow describe the invention in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

The following examples further illustrate the invention.

EXAMPLE 1

Physical Properties of TV-markers

Solid Phase Synthesis

Seven molecular weight markers were made with molecular weights ranging from about 3700–12000 daltons in the laboratory of Prof. M. Fridkin (Weizmann Institute of Science) (Table 2). These markers are referred to as TV-markers. The individual peptides were assigned a name TV-##, where ## is the number of amino acid residues (e.g. TV-35 is the 35-mer marker). The amino acid composition of these markers meets glatiramer acetate specifications (Table 2).

TABLE 2

| | Ala | Glu | Tyr | Lys |
|---|---|---|---|---|
| TV-35 - Peptide with a molecular weight = 3757 daltons | | | | |
| Number of residues | 15 | 5 | 3 | 12 |
| Molar fraction | 0.429 | 0.143 | 0.086 | 0.343 |

TABLE 2-continued

| | Ala | Glu | Tyr | Lys |
|---|---|---|---|---|
| TV-45 - Peptide with molecular weight = 4790 daltons | | | | |
| Number of residues | 20 | 6 | 4 | 15 |
| Molar fraction | 0.444 | 0.133 | 0.089 | 0.333 |
| TV-56 - Peptide with a molecular weight = 6008 daltons | | | | |
| Number of residues | 24 | 8 | 5 | 19 |
| Molar fraction | 0.429 | 0.143 | 0.089 | 0.339 |
| TV-66 - Peptide with a molecular weight = 7040 daltons | | | | |
| Number of residues | 29 | 9 | 6 | 22 |
| Molar fraction | 0.439 | 0.136 | 0.091 | 0.333 |
| TV-77 - Peptide with a molecular weight = 8259 daltons | | | | |
| Number of residues | 33 | 11 | 7 | 26 |
| Molar fraction | 0.429 | 0.143 | 0.091 | 0.338 |
| TV-86 - Peptide with a molecular weight = 9220 daltons | | | | |
| Number of residues | 37 | 12 | 8 | 29 |
| Molar fraction | 0.430 | 0.140 | 0.093 | 0.337 |
| TV-109 - Peptide with a molecular weight = 11727 daltons | | | | |
| Number of residues | 46 | 15 | 10 | 38 |
| Molar fraction | 0.422 | 0.138 | 0.092 | 0.349 |

Figures 1, 1A, 2:
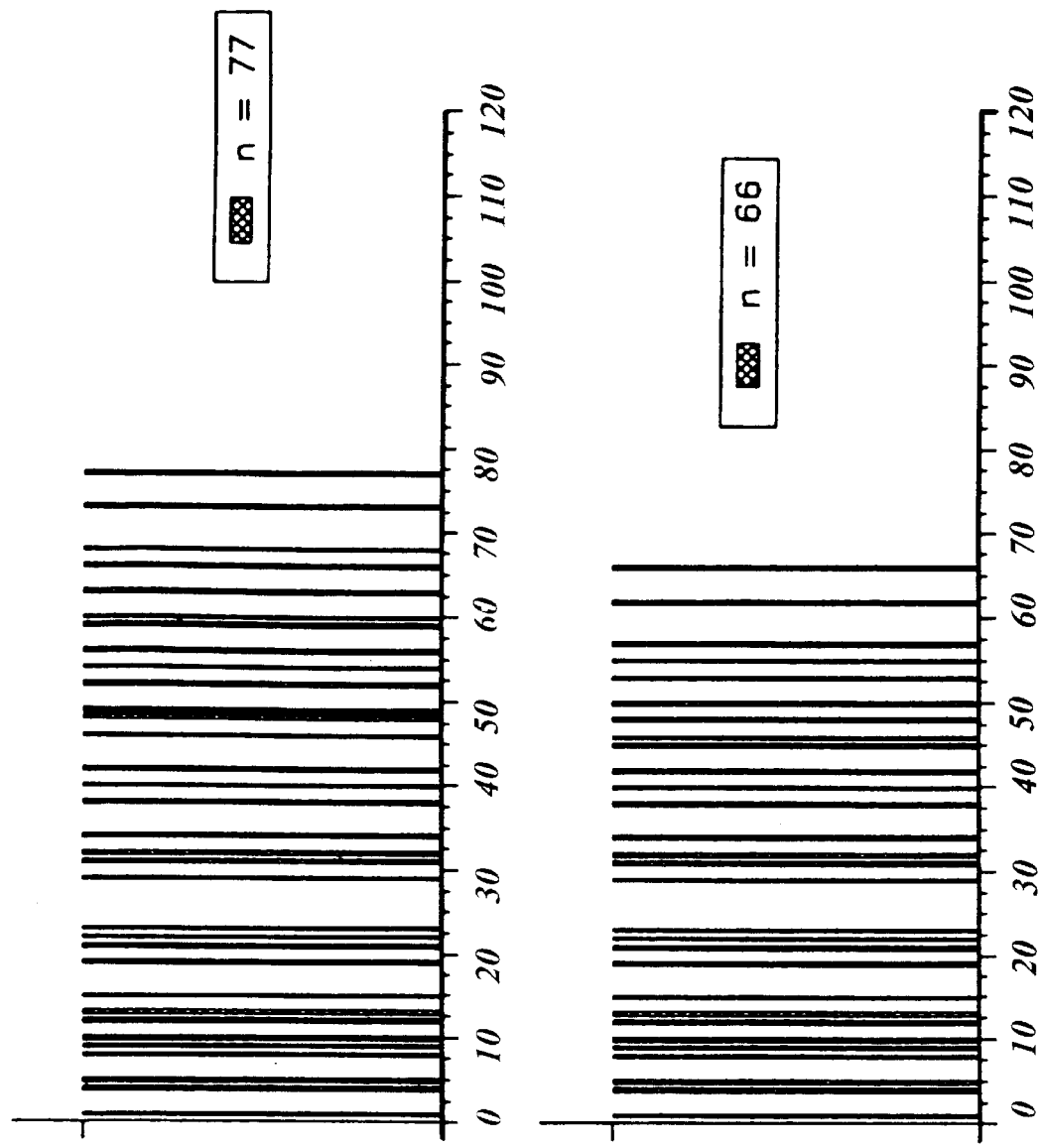
Figures 1, 1A, 2, 3:
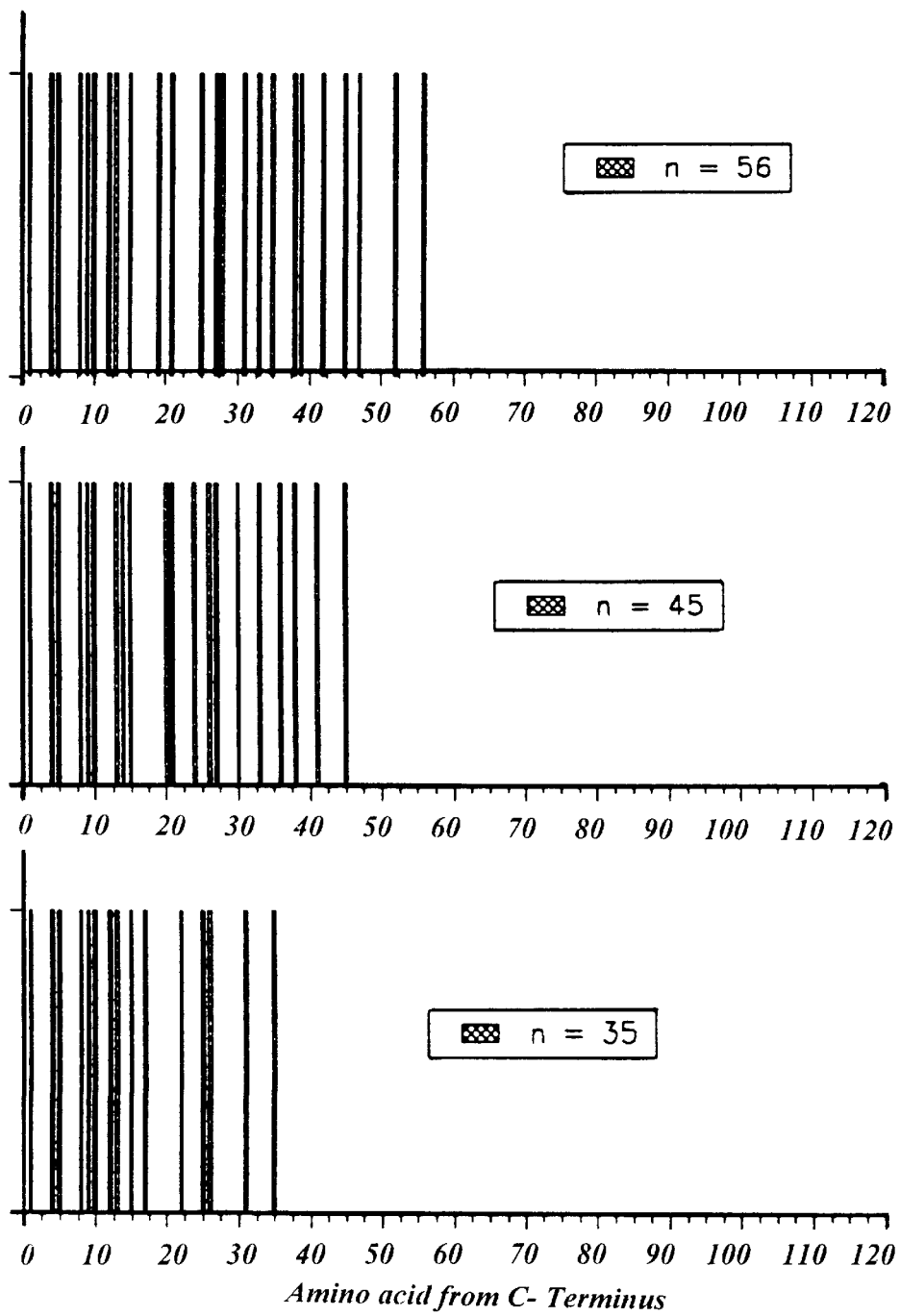
Figures 1, 1B:
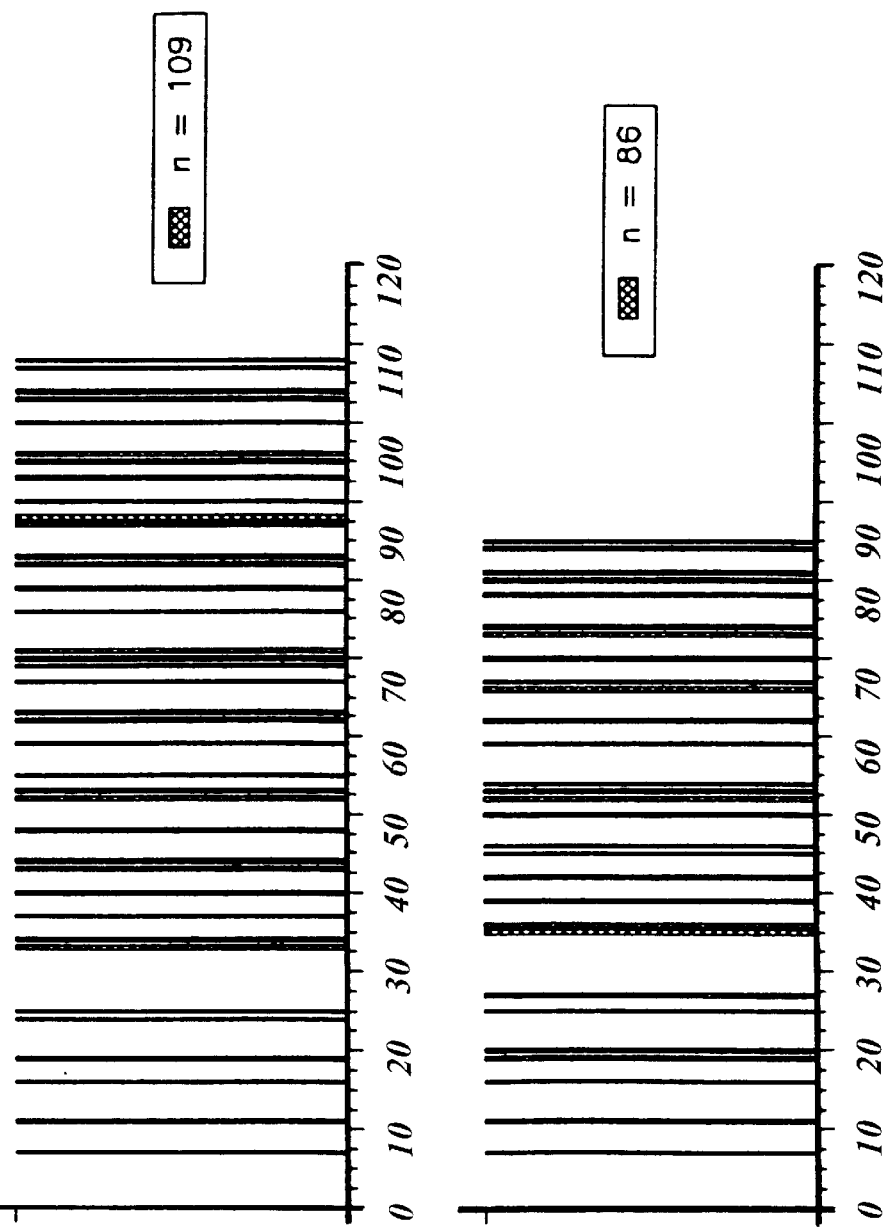
Figures 1, 1B, 2:
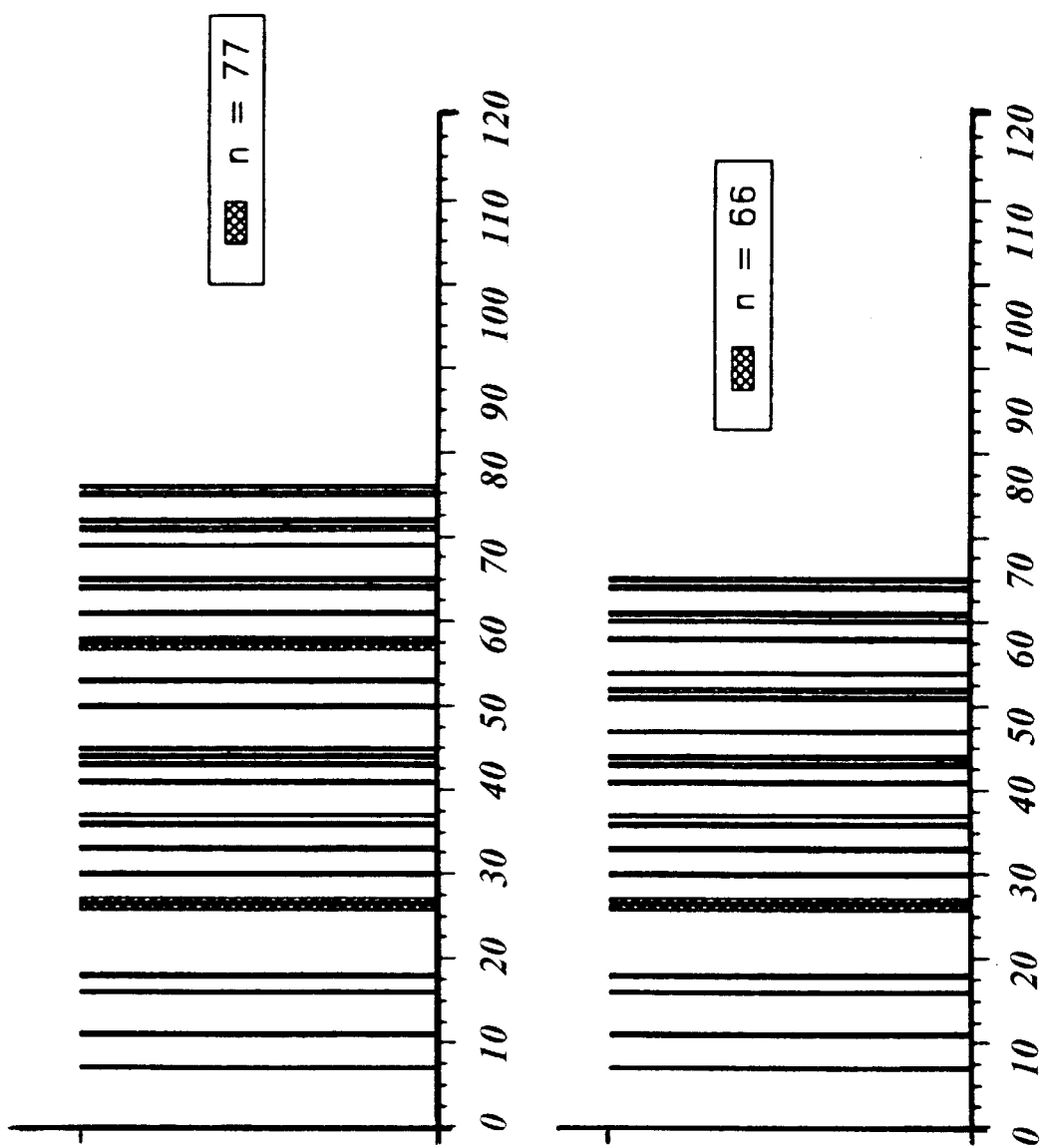
Figures 1, 1B, 2, 3:
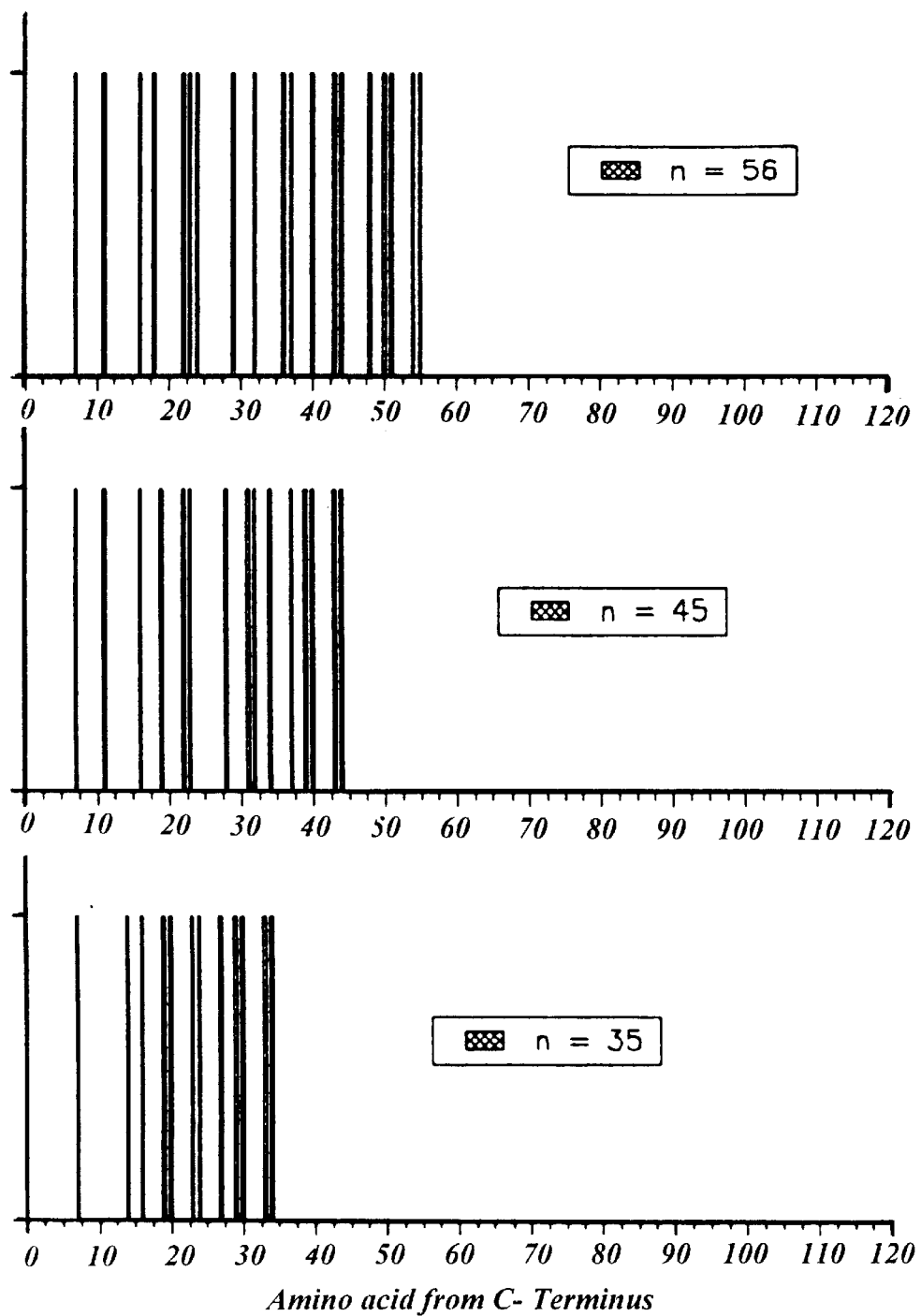
Figures 1, 1C:
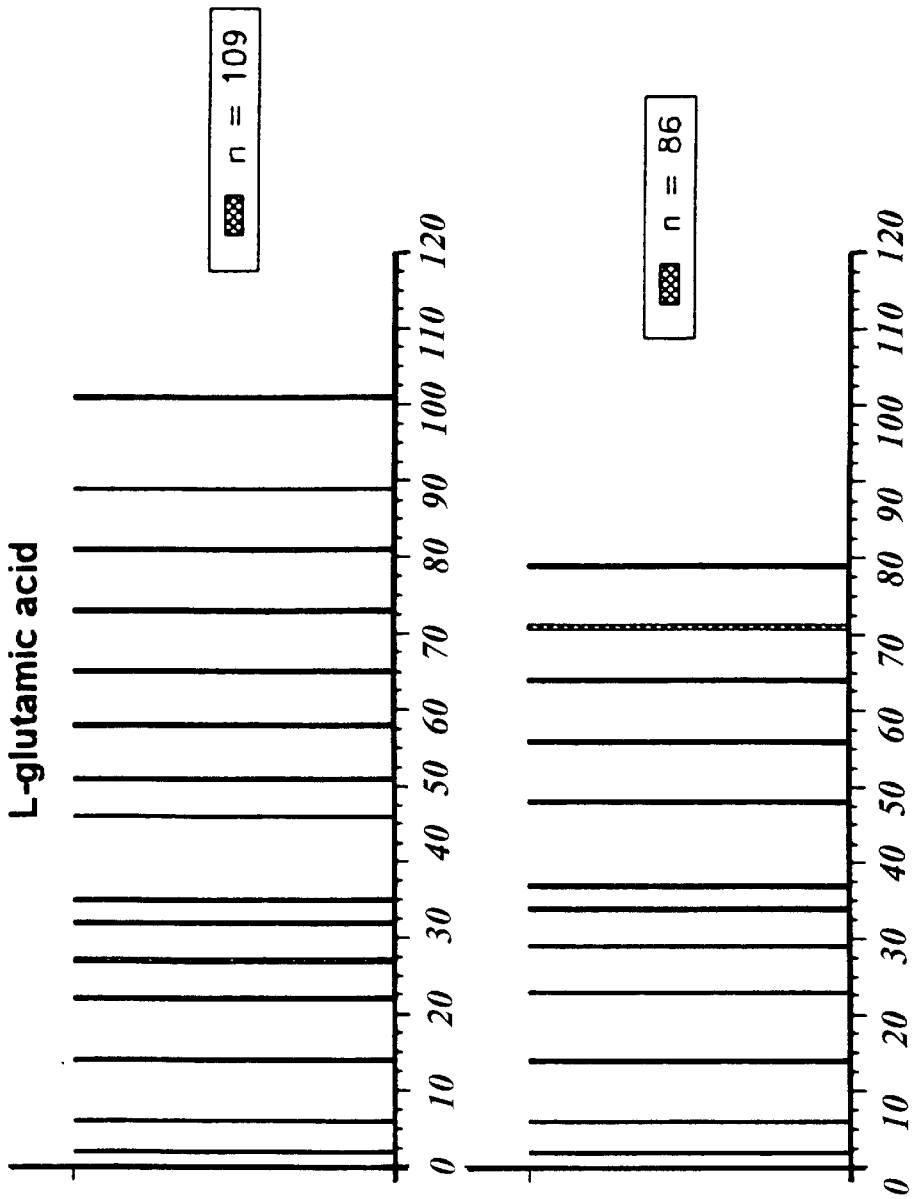
Figures 1, 1C, 2:
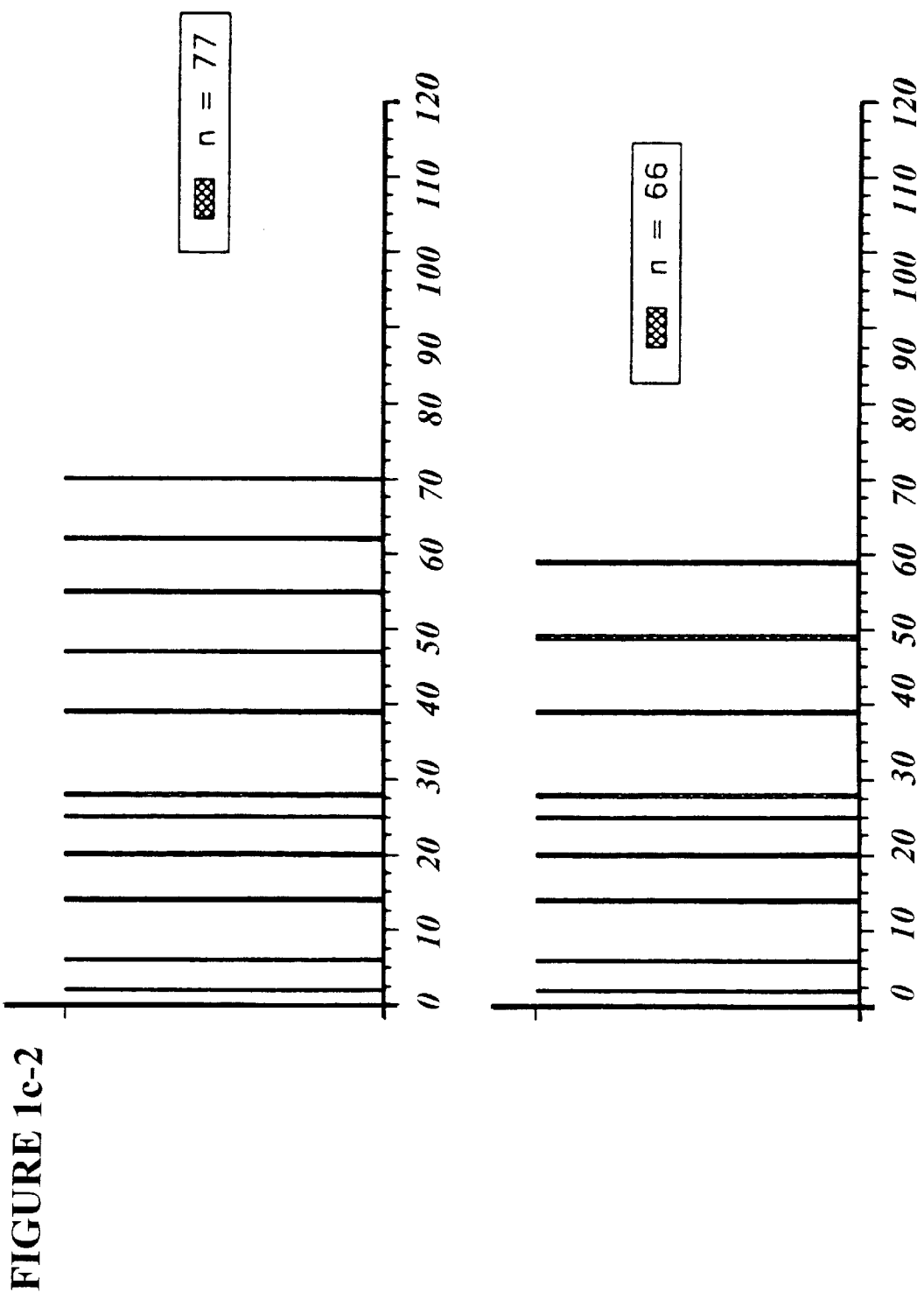
Figures 1, 1C, 2, 3:
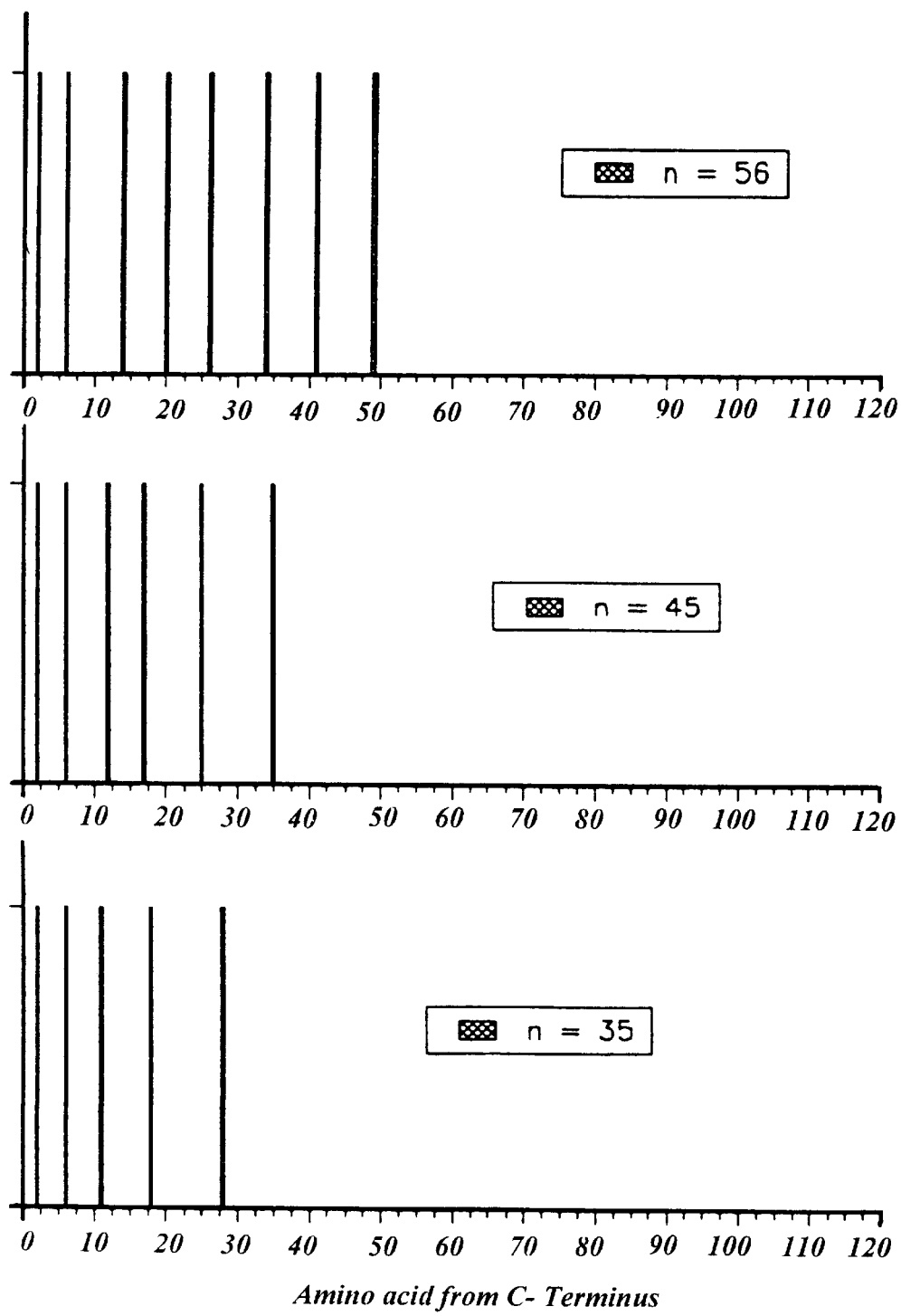
Figures 1, 1D:
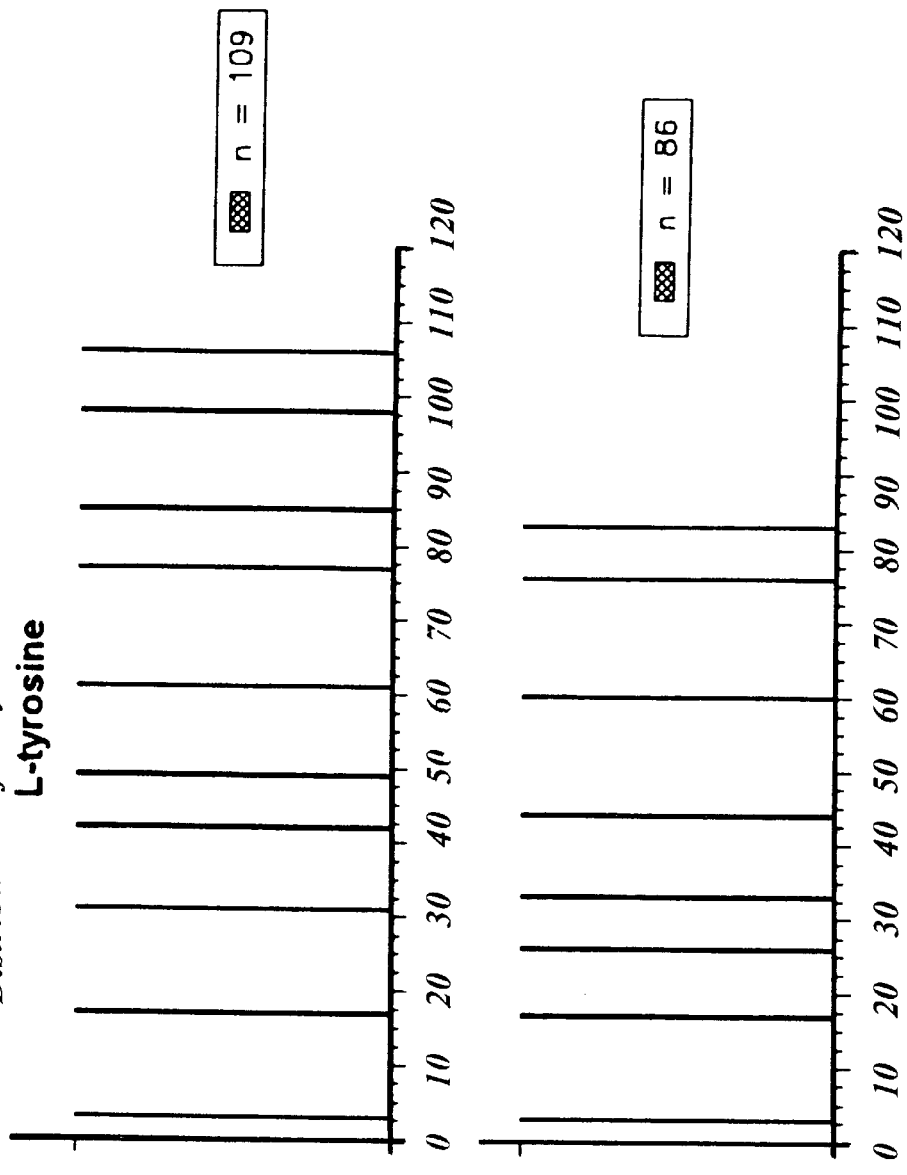
Figures 1, 1D, 2:
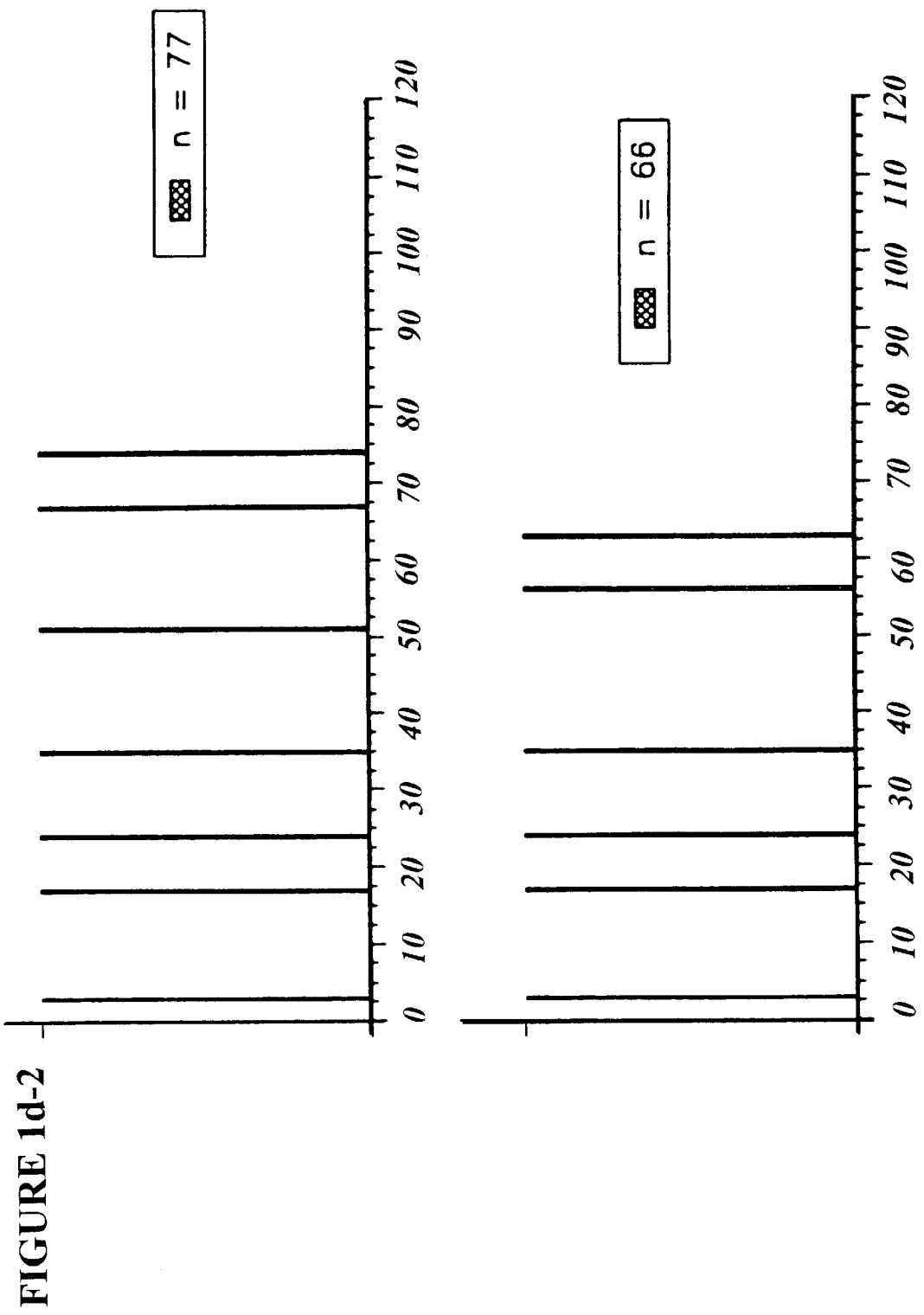
Figures 1, 1D, 2, 3:
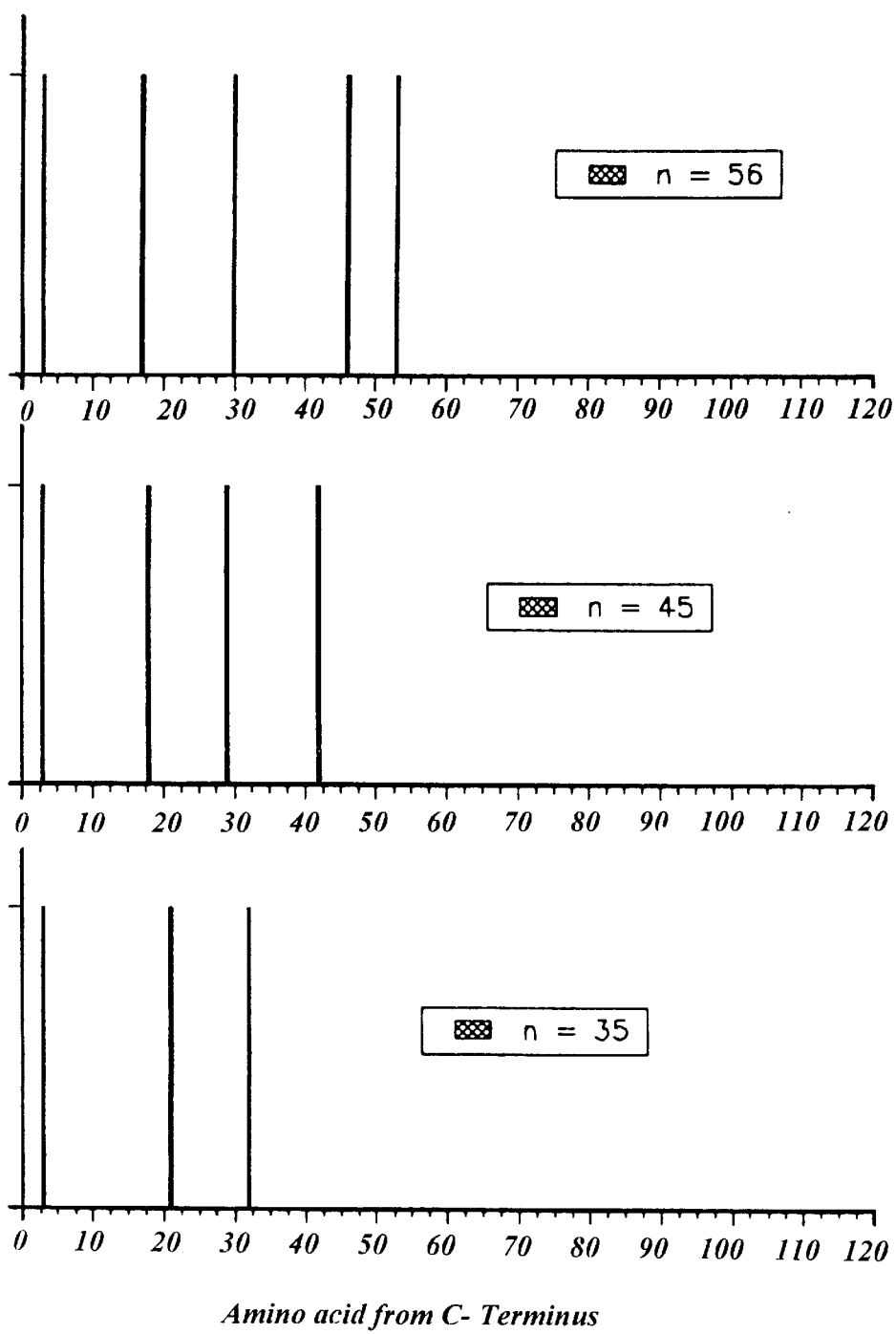
Figure 2:
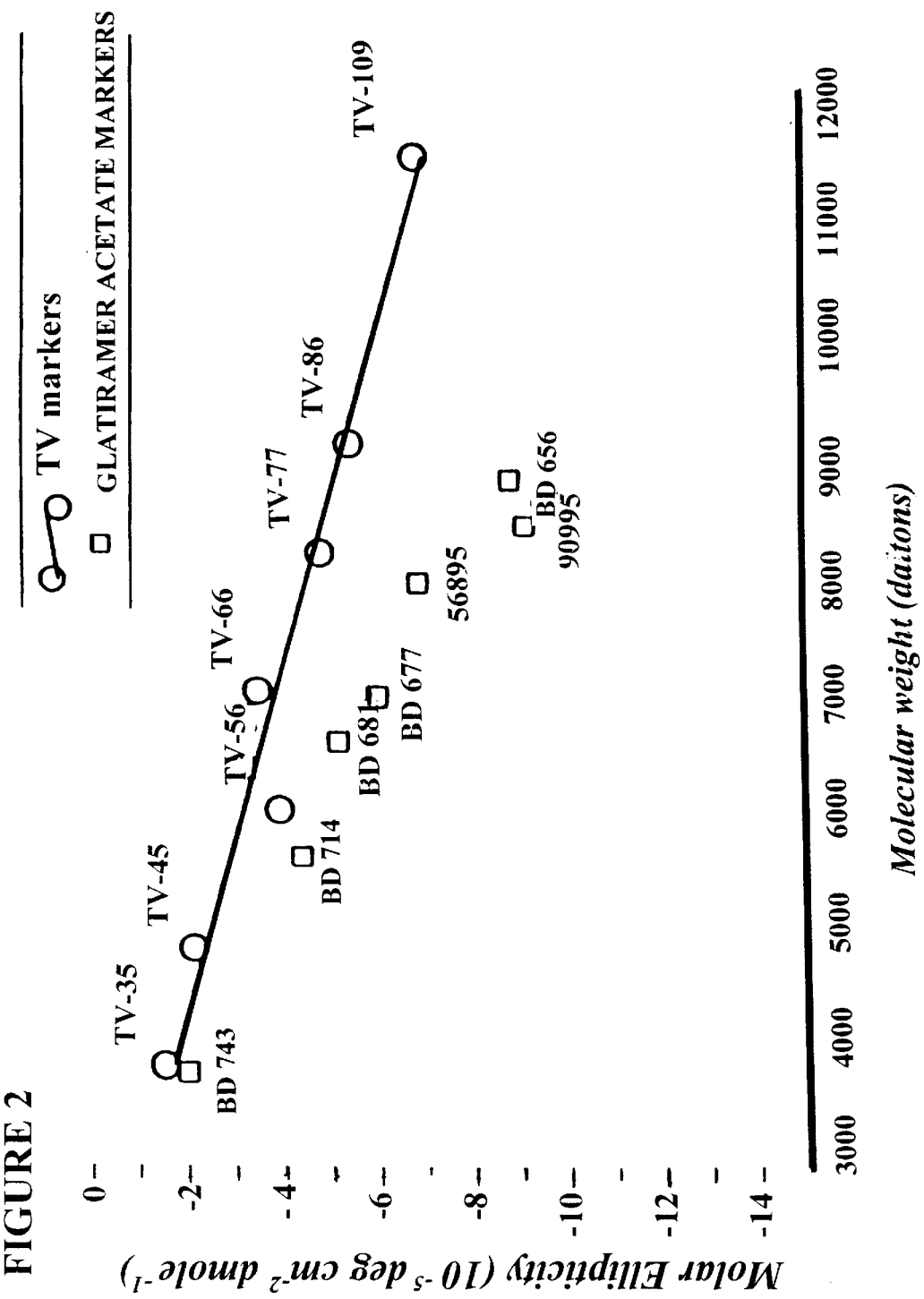

FIGS. 1$a$-1, 1$a$-2, 1$a$-3, 1$b$-1, 1$b$-2, 1$b$-3, 1$c$-1, 1$c$-2, 1$c$-3, 1$d$-1, 1$d$-2 and 1$d$-3 provide the distribution of alanine, lysine, glutamic acid and tyrosine, respectively, in the TV-markers described in Table 2. The amino acid position is defined by the X-axis, with the first amino acid corresponding to the C-terminal position. The presence of an amino acid is indicated by a vertical bar at the indicated amino acid position.

Confirmation of Mass and Sequence

Mass Spectroscopy—Polypeptide samples were analyzed immediately after their synthesis using a VG platform mass spectrophotometer equipped with an electronspray ion source. Several months later the analysis was repeated at TEVA using a PE-Sciex AP1300 mass spectrophotometer equipped with an electronspray ion source (Table 3, first preparation). These results indicate that each polypeptide TV-marker has a single, main component with the intended molecular mass.

TABLE 3

Mass Spectroscopy of Sequence-Defined Polypeptides

| Polypeptide | Designed molecular mass (daltons) | Determined molecular mass - first preparation (daltons) | Determined molecular mass - second preparation (daltons) |
|---|---|---|---|
| TV-35 | 3757 | 3757 | 3757 |
| TV-45 | 4790 | 4790 | 4790 |
| TV-56 | 6008 | 6008 | 6008 |
| TV-66 | 7040 | 7041 | 7040 |
| TV-77 | 8259 | 8259 | 8259 |
| TV-86 | 9220 | 9220 | 9220 |
| TV-109* | 11727 | 11728 | 11727 |

*The 109-mer was further purified by fractionation on a reversed-phase column. Three fractions were collected and fraction number 2 was designated for calibration purposes and referred to as TV-109.

A second batch of markers was prepared. Mass spectroscopy confirmed that the polypeptides of the second preparation were identical to the polypeptides of the first preparation (Table 3, second preparation). The similarity between the two preparations was also confirmed by chromatography on Superose 12. Each of the markers eluted with a sharp peak at a distinct retention time, regardless of the batch analyzed. Hence, the TV-markers of the present invention can be synthesized with reproducible mass.

Edman degradation—The intended sequence of the polypeptides was confirmed by Edman degradation analysis of the first preparation.

Characterization of the Polypeptides

Circular dichroism—Structural similarity between the molecular weight markers and glatiramer acetate is a prerequisite for an appropriate calibration of a molecular sizing column. Differences in polypeptide structure may result in different hydrodynamic size and consequently in altered retention time in the chromatographic system. The ellipticity, determined by circular dichroism, serves as a measure of the secondary structure of a polypeptide. When the ellipticity of the molecular weight markers and glatiramer acetate is similar, the structures of the two will be similar.

The molar ellipticity of the polypeptides was determined on a Jobin-Yvon CD spectrophotometer. FIG. 2 and Table 4 show that the extent of molar ellipticity correlated with the molecular weight of the polypeptide. The shortest peptide exhibited the lowest ellipticity value. The molar ellipticity of the new markers was of the same order of magnitude as those of the currently used glatiramer acetate molecular weight markers. Note that while the exact molecular weight for the TV-markers was plotted, the average-by-number molecular weight for the glatiramer acetate was used in the plot.

Thus, the new markers and glatiramer acetate possess similar structures and are therefore suitable for use as molecular weight markers for new preparations of glatiramer acetate.

TABLE 4

Molecular Ellipticity

| MW marker | MW (daltons) | M-ellip. (210 nm) |
|---|---|---|
| TV-markers | | |
| TV-35 | 3757 | −1.5367 |
| TV-45 | 4790 | −2.1651 |
| TV-56 | 6008 | −3.9658 |
| TV-66 | 7040 | −3.5172 |
| TV-77 | 8259 | −4.8365 |
| TV-86 | 9220 | −5.4546 |
| TV-109 | 11727 | −6.818 |
| glatiramer acetate | | |
| BD 743 | 3700 | −2.0186 |
| BD 714 | 5600 | −4.4182 |
| BD 681 | 6600 | −5.2019 |
| BD 677 | 7000 | −6.0153 |
| 56895 | 8000 | −6.9062 |
| 90995 | 8500 | −9.1736 |
| BD 656 | 8900 | −8.8576 |

These analytical data indicate that the synthesized TV-marker polypeptides exhibit a substantial degree of similarity to the currently used glatiramer acetate molecular weight markers. The amino acid content is within glatiramer acetate specifications. The new polypeptides and the glatiramer acetate molecular weight markers have similar secondary structure, expressed as molar ellipticity. Consequently, TV-markers are expected to migrate or elute in a gel permeation chromatographic (GPC) system, such as Superose 12, like a glatiramer acetate preparation.

EXAMPLE 2

Superose 12 Column Calibration with TV-markers

Figure 3A:
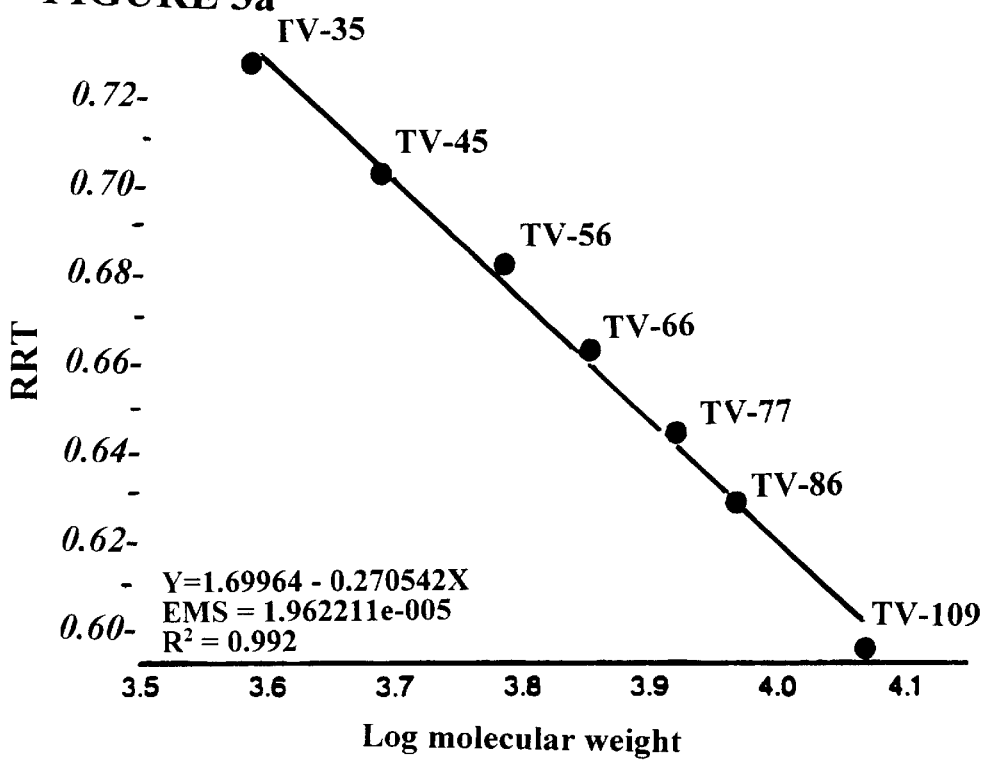
FIG. 3a provides a plot of the relative retention time (RRT) of the present TV-markers versus the log molecular weight of those markers, using the RRT-based algorithm.

TV-markers and a glatiramer acetate preparation are expected to demonstrate a similar correlation between relative retention time (RRT) and log molecular weight. The TV-markers were chromatographed on several Superose 12 columns. The peak retention time for each of the polypeptides was recorded. The linear correlation between Log Molecular Weight (MW) and the Relative Retention Time (RRT) was calculated as follows: RRT=B1+B2×Log MW (see FIG. 3a and Table 5).

Figure 3B:
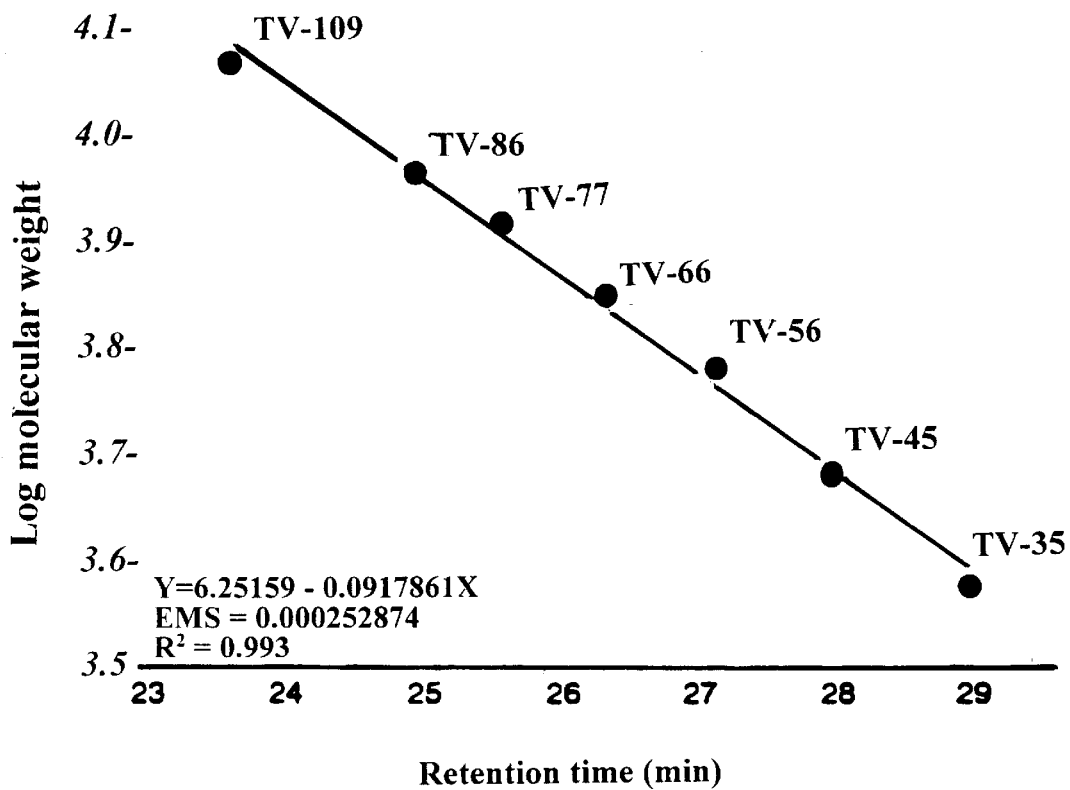
FIG. 3b provides a plot of the log molecular weight of the TV-markers versus the retention time (RT) of those markers, using the Millennium-based algorithm.

The recently introduced Millennium-based data acquisition system (Waters Corp., Milford, Mass.) provides integrated calibration of GPC columns. The algorithm for the calibration is based on the retention time and is given by the equation:

$$\text{Log } MW = A + B \times RT \text{ or } MW = 10^{(A+B \times RT)}$$

where MW is the molecular weight, RT is the retention time, A and B, respectively, are the intercept and the slope of the calculated regression function (FIG. 3b, Table 5).

The results obtained by this algorithm are practically identical to those obtained with the currently applied algorithm, based on RRT. In the effort to automate procedures, the Millennium-based data acquisition system was employed to perform the calibration using the TV-markers. The analytical methods were updated accordingly.

A good correlation ($r^2 > 0.98$) was obtained between log MW and RRT, although the points do not distribute evenly around the regression line. This distribution is due to the differences in the ellipticity of the various markers, as is also observed for the glatiramer acetate. The somewhat deviant-from-linearity low molecular weight marker cannot be excluded because the regression must cover values down to 2500 daltons for the first standard deviation (+1SD) distribution parameter. This is a general trait of all shorter peptides—they are less helical and more linear.

For the calibration based on the glatiramer acetate molecular weight markers, the intercept (B1) and slope (B2) were, respectively, 1.7415 and −0.2784. This compares favorably with the calibration values obtained with TV-markers (B1=1.6996; B2=−0.2705). The molecular weights obtained using the two calibration sets within the specification range differed by, typically, not more than 20% in the low molecular weight range and by not more than 12% in the RRT specification range of the peak (average molecular weight). This relatively small difference supports the claim that these markers can replace the currently used glatiramer acetate molecular weight markers without significant change in the reported molecular weight values.

TABLE 5a

Calibration by glatiramer acetate MW-markers

| Marker | MW | LOG MW | PEAK RT | RRT* |
|---|---|---|---|---|
| TV-35 | 3757 | 3.575 | 28.97 | 0.728 |
| TV-45 | 4790 | 3.68 | 27.96 | 0.703 |
| TV-56 | 6008 | 3.779 | 27.12 | 0.682 |
| TV-66 | 7040 | 3.848 | 26.32 | 0.662 |
| TV-77 | 8259 | 3.917 | 25.56 | 0.643 |
| TV-86 | 9220 | 3.965 | 24.93 | 0.627 |
| TV-109 | 11727 | 4.069 | 23.57 | 0.593 |
| INTERCEPT | **A | 6.2516 | ***B1 | 1.6996 |
| SLOPE | B | −0.0918 | B2 | −0.2705 |
| $r^2$ | | 0.9927 | | 0.9923 |

*RRT = RT/RTAcetone
**calculated according Millennium equation: log MW = A + B × RT
***calculated according to equation: RRT = $B_1 + B_2$ × log MW Calibration based on TV-markers was compared to calibration based on glatiramer acetate molecular weight markers (Table 5b). The two calibrations were compared by calculating molecular weight values for each calibration set in the RRT range of 0.5 to 0.8. The TV-marker calibration set included a fraction of TV-109 which was purified by reversed phase chromatography prior to use for column calibration.

TABLE 5b

Column Calibration by TV-markers

| RRT | RT* (min) | Glatir. Ac. (MW1) Daltons | TV (0.1) (MWm) Daltons | Difference (MWm−MW1) Daltons | % |
|---|---|---|---|---|---|
| 0.5 | 19.89 | 28800 | 26700 | −2100 | −7.3% |
| 0.51 | 20.28 | 26500 | 24500 | −2000 | −7.5% |
| 0.52 | 20.68 | 24400 | 22600 | −1800 | −7.4% |
| 0.53 | 21.08 | 22500 | 20700 | −1800 | −8.0% |
| 0.54 | 21.48 | 20700 | 19100 | −1600 | −7.7% |
| 0.55 | 21.87 | 19000 | 17500 | −1500 | −7.9% |
| 0.56 | 22.27 | 17500 | 16100 | −1400 | −8.0% |
| 0.57 | 22.67 | 16100 | 14800 | −1300 | −8.1% |
| 0.58 | 23.07 | 14900 | 13600 | −1300 | −8.7% |
| 0.59 | 23.46 | 13700 | 12500 | −1200 | −8.8% |
| 0.6 | 23.86 | 12600 | 11500 | −1100 | −8.7% |
| 0.61 | 24.26 | 11600 | 10600 | −1000 | −8.7% |
| 0.62 | 24.66 | 10700 | 9700 | −1000 | −9.3% |
| 0.63 | 25.06 | 9800 | 9000 | −800 | −8.2% |
| 0.64 | 25.45 | 9000 | 8200 | −800 | −8.9% |
| 0.65 | 25.85 | 8300 | 7600 | −700 | −8.4% |
| 0.66 | 26.25 | 7700 | 7000 | −700 | −9.1 |
| 0.67 | 26.65 | 7100 | 6400 | −700 | −9.9 |
| 0.68 | 27.04 | 6600 | 6900 | −600 | −9.2 |
| 0.69 | 27.44 | 6000 | 5400 | −600 | −10.0% |
| 0.70 | 27.84 | 5500 | 5000 | −500 | −9.1% |
| 0.71 | 28.24 | 5100 | 4600 | −500 | −9.8% |
| 0.72 | 28.63 | 4700 | 4200 | −500 | −10.6% |
| 0.73 | 29.03 | 4300 | 3900 | −400 | −9.3% |
| 0.74 | 29.43 | 4000 | 3600 | −400 | −10.0% |
| 0.75 | 29.83 | 3600 | 3300 | −300 | −8.3% |
| 0.76 | 30.23 | 3400 | 3000 | −400 | −11.8% |
| 0.77 | 30.62 | 3100 | 2800 | −300 | −9.7% |
| 0.78 | 31.02 | 2800 | 2500 | −300 | −10.7% |
| 0.79 | 31.42 | 2600 | 2300 | −300 | −11.5% |
| 0.80 | 31.82 | 2400 | 2100 | −300 | −12.5% |

Purity of TV markers—Three of the markers (TV-66, TV-77 and TV-86) were further purified by reversed phase chromatography. Three fractions were obtained for each marker. The middle fraction containing the major portion of the peak was chromatographed on the Superose 12 system in comparison to the unfractionated markers (Table 6). TV markers were size chromatographed without purification (Regular) and after purification by reversed-phase chromatography (Purified). Peak retention times were determined and the differences were calculated. The peak retention time remained unaffected by the degree of purity. Therefore, the final product of the synthesis is useful for accurate calibration and extra purification is not required.

TABLE 6

Effect of Purification on Retention Time

| | Retention Time (RT) (min) | | Difference |
|---|---|---|---|
| TV-marker | Regular | Purified | (%) |
| TV-66 | 26.200 | 26.233 | −0.13% |
| TV-77 | 25.450 | 25.450 | 0.00% |
| TV-86 | 24.867 | 24.850 | 0.07% |

Consistency in reported values (Cross-validation)—Six batches of glatiramer acetate, manufactured in 1993 and 1994, were reanalyzed by GPC calibrated with the TV-markers. Their average molecular weight and the molecular weight distribution was compared to the values reported at the time of their release. Table 7 shows a comparison of molecular weight data from the original certificate of analysis and molecular weight data obtained using a Superose 12 column calibrated with TV-markers. The differences in reported values are typically less than 10%.

TABLE 7

Comparison of Molecular Weight Determinations

| Cop 1 preparation | | MW Millennium | MW CoA | % difference |
|---|---|---|---|---|
| 00193 | average | 10250 | 9900 | -3.5% |
| | -1 SD | 20950 | 19100 | -9.7% |
| | +1 SD | 51000 | 4800 | -6.3% |
| 00594 | average | 6700 | 6550 | -2.3% |
| | -1 SD | 15700 | 15100 | -4.0% |
| | +1 SD | 3600 | 3400 | -5.9% |
| 00993 | average | 9200 | 8600 | -7.0% |
| | -1 SD | 18500 | 17350 | -6.9% |
| | +1 SD | 4700 | 4400 | -6.8% |
| 04194 | average | 6100 | 6150 | 0.8% |
| | -1 SD | 12600 | 12500 | -0.8% |
| | +1 SD | 3200 | 3200 | 0.0% |
| 01793 | average | 8800 | 8300 | -6.0% |
| | -1 SD | 18100 | 17300 | -4.6% |
| | +1 SD | 5200 | 4750 | -9.5% |
| 05494 | average | 8100 | 8300 | 2.4% |
| | -1 SD | 17800 | 17450 | -2.0% |
| | +1 SD | 4100 | 4100 | 0.0% |

Stability of markers in solution—TV-markers were chromatographed four times over a period of 24 hours. All markers were kept as solutions at room temperature and were analyzed at 8 hour intervals. Table 8 shows the peak retention time measures for the TV-markers at each of the four time points. At a concentration of 0.1 mg/ml, the TV-markers were stable in solution for at least 24 hours at room temperature.

TABLE 8

Stability of TV-markers in solution at room temperature.

| | Peak Retention Time (min) | | | | Average | RSD |
|---|---|---|---|---|---|---|
| TV-35 | 29.883 | 29.883 | 29.900 | 29.950 | 29.904 | 0.106% |
| TV-45 | 28.933 | 28.917 | 28.917 | 28.933 | 28.925 | 0.032% |
| TV-56 | 28.250 | 28.217 | 28.283 | 28.250 | 28.250 | 0.095% |
| TV-66 | 27.400 | 27.350 | 27.433 | 27.433 | 27.404 | 0.143% |
| TV-77 | 26.750 | 26.700 | 26.750 | 26.783 | 26.746 | 0.128% |
| TV-86 | 26.117 | 26.100 | 26.150 | 26.150 | 26.129 | 0.095% |
| TV-109Fr11 | 24.783 | 24.850 | 24.883 | 24.850 | 24.842 | 0.169% |

In addition, solutions of the markers were stored for up to 3½ months under various storage conditions (2–8° C., –10 to –20° C., with/without azide). TV-markers are stable for at least 3 months when stored as frozen solutions (Table 9). As a precaution it was decided to allow storage of frozen solutions for two months.

Lyophilized TV-markers are stable for at least two years according to accumulated stability data.

TABLE 9

Stability of TV-markers at –10° to –20° C.

| | | Date of calibration: | | |
|---|---|---|---|---|
| | | May 22, 1997 | Jul. 09, 1997 | Sep. 04, 1997 |
| Interval (days) | | — | 48 | 105 |
| Marker | MW | RT | RT | RT |
| TV-35 | 3757 | 28.867 | 28.867 | 28.967 |
| TV-45 | 4790 | 27.833 | 27.917 | 27.950 |
| TV-56 | 6008 | 27.076 | 27.133 | 27.100 |
| TV-66 | 7040 | 26.233 | 26.317 | 26.300 |
| TV-77 | 8259 | 25.467 | 25.617 | 25.550 |
| TV-86 | 9220 | 24.883 | 25.017 | 24.950 |
| TV-109 | 11727 | 23.500 | 23.650 | 23.583 |

Figure 4A:
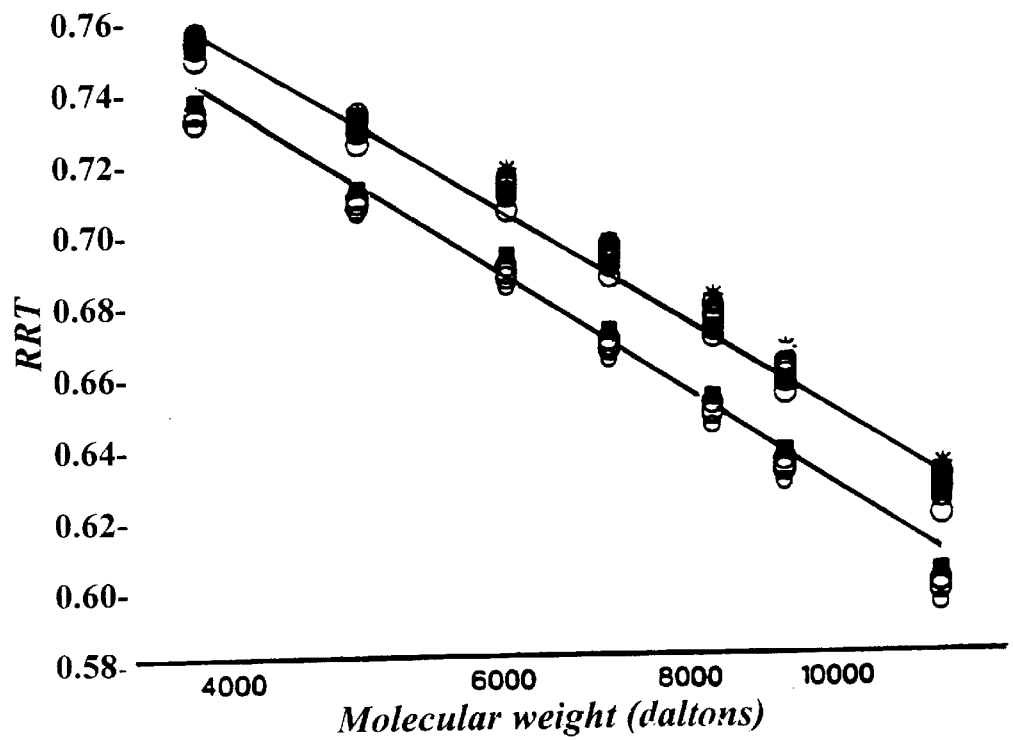
FIG. 4a provides a plot summarizing several calibrations of the relative retention time (RRT) of the present TV-markers versus the molecular weight of those markers, using the RRT-based algorithm. Data were obtained from sixteen columns. Average values for each of the sixteen calibrations are depicted.
Figure 4B:
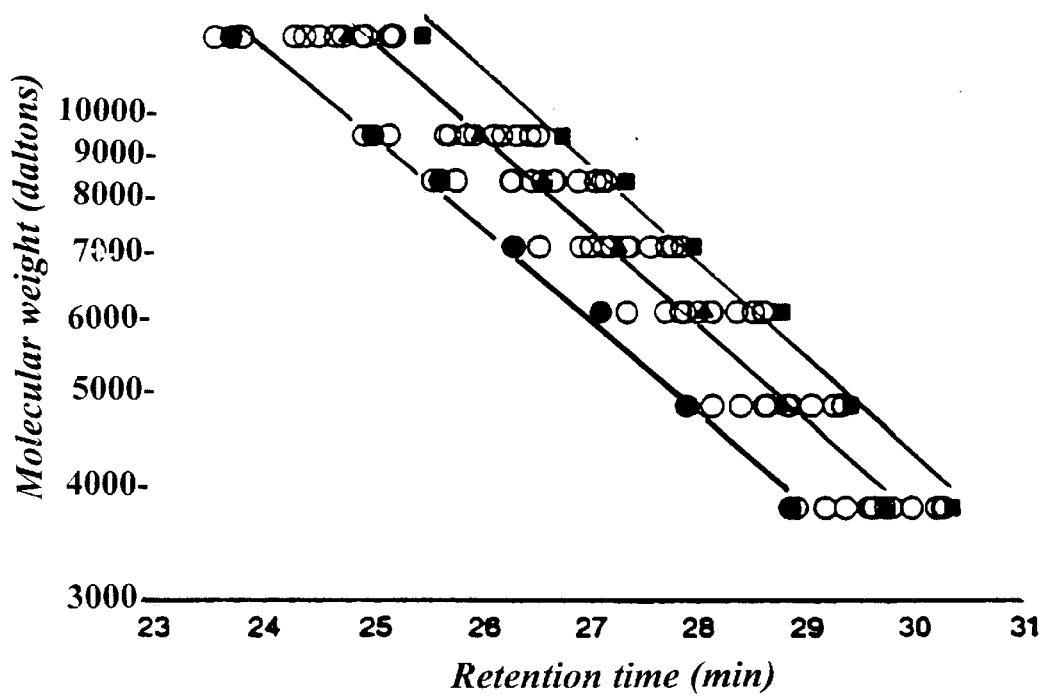
FIG. 4b provides a plot summarizing several calibrations of the molecular weight of the TV-markers versus the relative retention time (RRT) of those markers, using the Millennium-based algorithm. Data were obtained from sixteen columns. Average values for each of the sixteen calibrations are depicted.
Figure 5:
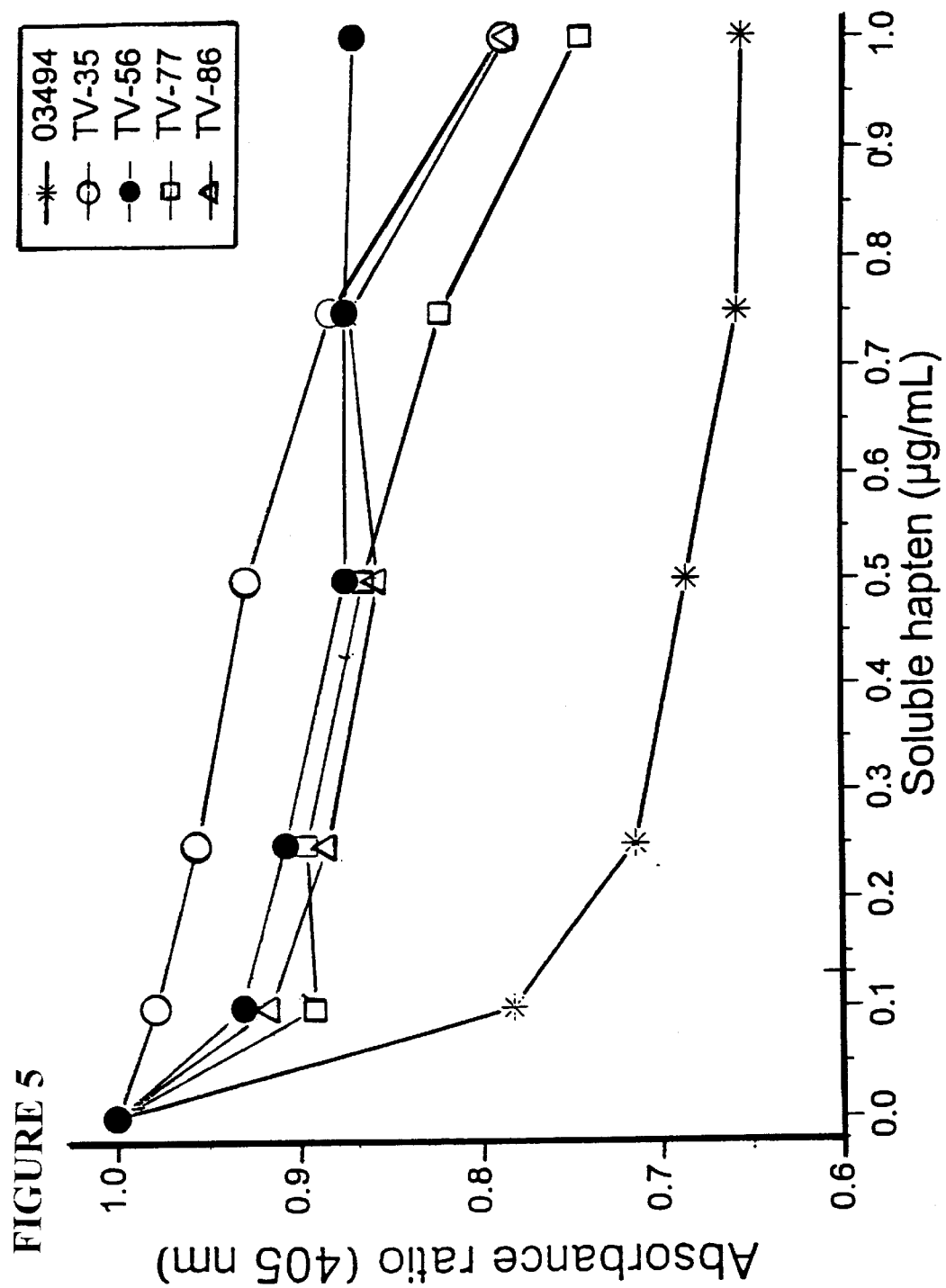
FIG. 5 depicts inhibition of Cop 1 binding to anti-Cop 1 polyclonal antibodies by four TV-markers and Cop 1 (03494). Absorbance ratio indicates absorbance measured with increasing inhibitor concentration relative to absorbance in the absence of binding inhibition.

Summary of calibration data—Overall, the TV-markers were analyzed 53 times in two laboratories. A summary of the data is presented in FIG. 4 and Table 10. The differences observed among the individual runs (FIG. 4) reflect variations between columns rather than differences between the participating laboratories. This is indicated in FIG. 4 by the use of different symbols for some of the runs. Calibration constants in Table 10 were calcualted using the Millennium equation for data obtained for 53 calibration sets injected into 16 columns.

TABLE 10

Calibration constants obtained in Plantex and Abic Labs

| | | RT | | | | | RT | |
|---|---|---|---|---|---|---|---|---|
| | | | | | | | Mean – | Mean + |
| Marker | MW | Mean | SD | RSD % | Min | Max | SD | SD |
| TV-35 | 3757 | 29.69 | 0.463 | 1.6% | 28.85 | 30.35 | 28.30 | 31.08 |
| TV-45 | 4790 | 28.72 | 0.481 | 1.7% | 27.88 | 29.40 | 27.28 | 30.16 |
| TV-56 | 6008 | 27.99 | 0.520 | 1.9% | 27.08 | 28.77 | 26.43 | 29.55 |
| TV-66 | 7040 | 27.19 | 0.526 | 1.9% | 26.26 | 27.96 | 25.61 | 28.77 |
| TV-77 | 8259 | 26.49 | 0.550 | 2.1% | 25.51 | 27.33 | 24.84 | 28.14 |
| TV-6 | 9220 | 25.89 | 0.556 | 2.1% | 24.89 | 26.72 | 24.22 | 27.56 |
| TV-109 | 11727 | 24.56 | 0.557 | 2.3% | 23.53 | 25.41 | 22.89 | 26.23 |
| Intercept (A) | | 6.4706 | 0.1220 | 1.9% | 6.2561 | 6.6500 | 6.1046 | 6.8366 |
| Slope (B) | | -0.0969 | 0.0032 | -3.3% | -0.1014 | -0.0919 | -0.1064 | -0.0873 |
| $r^2$ | | 0.9901 | 0.0022 | 0.2% | 0.9868 | 0.9828 | 0.9835 | 0.9967 |

Molecular weight distribution of a glatiramer acetate preparation—Molecular weight was determined for a batch of glatiramer acetate (BN 90995). Table 11 summarizes data obtained from 16 determinations on TV-marker-calibrated columns.

TABLE 11a

RT of glatiramer acetate (BN 90995)

| | Average | SD | RSD% |
|---|---|---|---|
| Peak | 26.208 | 0.434 | 1.66 |
| −2SD (2.5%) | 19.865 | 0.528 | 2.66 |
| −1SD (16%) | 22.578 | 0.477 | 2.11 |
| +1SD (84%) | 28.934 | 0.324 | 1.12 |

TABLE 11b

RRT of glatiramer acetate (BN 90995)

| | Average | SD | RSD% |
|---|---|---|---|
| Peak | 0.664 | 0.014 | 2.09 |
| −2SD (2.5%) | 0.503 | 0.016 | 3.09 |
| −1SD (16%) | 0.572 | 0.015 | 2.54 |
| +1SD (84%) | 0.733 | 0.011 | 1.53 |

TABLE 11c

MW (Daltons) of glatiramer acetate (BN 90995)

| | Average | SD | RSD% |
|---|---|---|---|
| Peak | 7459 | 146 | 1.95 |
| −1SD (16%) | 16622 | 466 | 2.80 |
| +1SD (84%) | 4089 | 77 | 1.89 |

The application of a molecular weight and sequence-defined set of markers for the calibration of the Superose 12 column has several advantages over the currently used glatiramer acetate molecular weight markers.

First, the use of solid phase synthesis assures consistency among the various preparations of each batch. Mass spectroscopy results (Table 3) confirmed the reproducibility of the synthesis. This consistency provides improved accuracy in molecular weight determinations.

Second, the current calibration is based on the determination of the RRT at 50% of the peak area for each of the glatiramer acetate molecular weight markers. The new markers elute as sharp peaks. Their use in calibration is more accurate than the calculated retention time at 50% of the area of a broad peak.

Third, the use of markers having molecular weights defined by predetermined sequence precludes any uncertainty which might accompany the use of markers whose molecular weight is determined by inexact measurement of physical properties.

Fourth, the calibration procedure facilitates normalization of columns for molecular weight determinations, regardless of minor changes between column lots, age or instrumentation.

EXAMPLE 3

Biological Activity of TV-markers

Reactivity of TV-markers with monoclonal antibodies to Cop 1.—Table 12 shows the binding of anti-Cop 1 monoclonal antibodies to TV-markers. TV-markers and reference Glat production batches were tested. Microtiter wells were coated with 2 μg/ml antigen. Values are counts per minute (cpm) of $^{125}$I-goat anti-mouse IgG bound to the monoclonal antibodies. Antibody binding to each TV-marker is compared to antibody binding to Cop 1 reference standard.

TABLE 12

Reactivity of TV-markers and Cop 1 with mAbs in RIA

| | Binding of mAb cpm (% Cop 1 binding) | | |
|---|---|---|---|
| Coating Antigen | anti-Cop-1 (3-3-9) | anti-Cop-1 (3-1-45) | anti-Cop-1 (5-7-2) |
| PBS | 1384 | 315 | 521 |
| 03494 (glatiramer acetate) | 14860 | 20587 | 10513 |
| 55296 (glatiramer acetate) | 13705 (91) | 17189 (83) | 8683 (82) |
| 55396 (glatiramer acetate) | 13458 (90) | 17564 (85) | 9142 (86) |
| TV-35 (TV-marker) | 1176 (0) | 343 (0) | 657 (1) |
| TV-56 (TV-marker) | 1614 (2) | 1581 (6) | 9584 (91) |
| TV-77 (TV-marker) | 2265 (6) | 2152 (9) | 4259 (37) |
| TV-86 (TV-marker) | 1625 (2) | 1606 (6) | 8140 (76) |

Reactivity with Cop 1 specific T cells.—T cells lines which can be stimulated with GLAT copolymer were used to test stimulatory activity of TV-markers in comparison to regular GLAT copolymer production batches (Table 13). As above, the activities of TV-markers were tested for in vitro. The proliferation of various mouse and human T cell lines was determined in response to peptides in culture. The cell lines included: BALB/c-Ts-Cop-1, a tempreature-sensitive line derived from BALB/c mice; L-22-1, a tempreature-sensitive clone derived from $F_1$ mice; SC-103 and SC-14: human Cop 1 specific T cell clones. Proliferation was determined by measuring $^3$H-thymidine uptake by the T cell lines cultured with 10 μg of GLAT copolymer or TV-marker.

Glatiramer acetate batches were stimulatory. TV-markers were also found to stimulate two of the four T cell lines, although not as strongly. TV-markers are recognized by both mouse and human T cells specific to glatiramer acetate. This confirms that there is amino acid sequence similarity and T cell epitope similarity among glatiramer acetate and TV-markers.

TABLE 13

Reactivity of glatiramer acetate and TV-markers with glatiramer acetate specific T cell lines

| | $^3$H-Thymidine incorporation cpm (% Cop 1) | | | |
|---|---|---|---|---|
| Antigen | BALB/c-Ts-Cop-1 | L-22-1 | SC-103 | SC-14 |
| PBS | 588 | 207 | 342 | 760 |
| 03494 (glatiramer acetate) | 32643 | 16395 | 8709 | 3091 |
| 55296 (glatiramer acetate) | 35820 (110) | 17315 (106) | 7148 (81) | 2973 (95) |
| 55396 (glatiramer acetate) | 34281 (105) | 17211 (105) | 7019 (80) | 3253 (107) |
| TV-35 (TV-marker) | 9465 (28) | 225 (0) | 438 (0) | 884 (0) |
| TV-56 (TV-marker) | 19545 (59) | 232 (0) | 237 (0) | 3495 (117) |

TABLE 13-continued

Reactivity of glatiramer acetate and TV-markers
with glatiramer acetate specific T cell lines

| Antigen | ³H-Thymidine incorporation cpm (% Cop 1) | | | |
|---|---|---|---|---|
| | BALB/ c-Ts-Cop-1 | L-22-1 | SC-103 | SC-14 |
| TV-77 (TV-marker) | 17367 (52) | 300 (1) | 327 (0) | 2701 (83) |
| TV-86 (TV-marker) | 14694 (44) | 418 (1) | 298 (0) | 2284 (65) |

Blocking of Experimental Allergic Encephalomyelitis—
To test the physiological activity of TV-markers, protection from experimental allergic encephalomyelitis (EAE) was investigated in mice. Injection of Copolymer 1 in complete Freund's adjuvant together with the encephalitogen can block EAE essentially as described in Aharoni et al., 17 Eur. J. Immunol. 23 (1993). Other researchers have observed that the therapeutic effect of Copolymer 1 in multiple sclerosis patients is also associated with the induction of $T_H2$ cells. Lahat et al., 244 J. Neurol. 129 (1997). In this example, EAE is blocked by different polypeptides of the present invention.

Induction of EAE—Two to three month old female (SJL/JxBALB/c)FI mice are injected in all four footpads with mouse spinal cord homogenate (3.5 mg/mouse) emulsified in a 1:1 ratio in complete Freund's adjuvant (CFA) supplemented with 4 mg/ml mycobacterium tuberculosis H37Ra. Pertussis toxin (0.25 ml, 250 ng, Sigma) is injected intravenously, immediately after and 48 hr later. Mice are examined daily from day 10 post induction for clinical signs of EAE which were scored on a 0–5 scale as described in Lando et al., 123 J. Immunol. 2156 (1979).

EAE blocking by injection with complete adjuvant—Each antigen being tested was included in the encephalitogenic inoculum. Table 14 shows the incidence of EAE in animals which received the encephalitogenic inoculum supplemented with a TV-marker or glatiramer acetate and in animals which received only the encephalitogenic inoculum. Also shown is the mean onset of EAE in animals which were not protected. Disease intensity is scored daily in mice with a score of zero (0=healthy) to five (5=dead). The onset is determined as the day an animal exhibits a disease score of at least one (1).

TABLE 14

Protection from EAE by TV-markers

| Blocking Antigen | Incidence | Mean Score | Mean Onset (days) | % Blocking |
|---|---|---|---|---|
| None (control) | 10/10 | 4.9 | 11.3 | — |
| TV-45 | 0/10 | 0 | — | 100 |
| TV-66 | 6/10 | 2.8 | 11.7 | 40 |
| TV-77 | 1/9 | 0.2 | 14.0 | 89 |
| TV-86 | 3/10 | 0.7 | 12.0 | 70 |
| TV-109 | 0/10 | 0 | — | 100 |
| 03494 | 0/10 | 0 | — | 100 |
| 55396 | 0/10 | 0 | — | 100 |

---

What is claimed:

1. A purified polypeptide having an amino acid sequence which is SEQ ID NO:1, SEQ ID NO:2, SEQ ID NO:3, SEQ ID NO:4, SEQ ID NO:5, SEQ ID NO:6 or SEQ ID NO:7.
2. The purified polypeptide of claim 1, wherein said polypeptide consists entirely of L-amino acids.
3. The purified polypeptide of claim 1, wherein said polypeptide consists entirely of D-amino acids.
4. The purified polypeptide of claim 1 having the amino acid sequence SEQ ID NO: 1.
5. The purified polypeptide of claim 1 having the amino acid sequence SEQ ID NO: 2.
6. The purified polypeptide of claim 1 having the amino acid sequence SEQ ID NO: 3.
7. The purified polypeptide of claim 1 having the amino acid sequence SEQ ID NO: 4.
8. The purified polypeptide of claim 1 having the amino acid sequence SEQ ID NO: 5.
9. The purified polypeptide of claim 1 having the amino acid sequence SEQ ID NO: 6.
10. The purified polypeptide of claim 1 having the amino acid sequence SEQ ID NO: 7.
11. A composition comprising a purified polypeptide of any one of claims 1, 2–3 or 4–10 and a carrier.
12. A composition consisting essentially of a mixture of purified polypeptides, wherein each polypeptide has the amino acid sequence SEQ ID NO:1, SEQ ID NO:2, SEQ ID NO:3, SEQ ID NO:4, SEQ ID NO:5, SEQ ID NO:6 or SEQ ID NO:7.

* * * * *

SEQUENCE LISTING

<160> NUMBER OF SEQ ID NOS: 7

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 1

Ala Lys Lys Tyr Ala Lys Lys Glu Lys Ala Ala Lys Lys Ala Tyr Lys
 1               5                  10                  15

Lys Glu Ala Lys Ala Lys Ala Ala Glu Ala Ala Ala Lys Glu Ala Ala
             20                  25                  30

Tyr Glu Ala
         35

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 2

Ala Lys Lys Tyr Ala Lys Lys Ala Lys Ala Glu Lys Ala Lys Lys Ala
 1               5                  10                  15

Tyr Lys Ala Ala Glu Ala Lys Lys Ala Lys Tyr Glu Lys Ala Ala
             20                  25                  30

Ala Glu Lys Ala Ala Ala Lys Glu Ala Ala Tyr Glu Ala
         35                  40                  45

<210> SEQ ID NO 3
<211> LENGTH: 56
<212> TYPE: PRT
<213> ORGANISM: Artificial Sequence
<220> FEATURE:
<223> OTHER INFORMATION: Description of Artificial Sequence:   SYNTHETIC
      PEPTIDE

<400> SEQUENCE: 3

Ala Lys Lys Tyr Ala Lys Lys Glu Lys Ala Tyr Ala Lys Lys Ala Glu
 1               5                  10                  15

Lys Ala Ala Lys Lys Ala Glu Ala Lys Ala Tyr Lys Ala Ala Glu Ala
             20                  25                  30

Lys Lys Lys Ala Glu Ala Lys Tyr Lys Ala Glu Ala Ala Lys Ala Ala
         35                  40                  45

Ala Lys Glu Ala Ala Tyr Glu Ala
         50                  55

<210> SEQ ID NO 4
<211> LENGTH: 66
<212> TYPE: PRT
<213> ORGANISM: Artificial Sequence
<220> FEATURE:
<223> OTHER INFORMATION: Description of Artificial Sequence:   SYNTHETIC
      PEPTIDE

<400> SEQUENCE: 4

Ala Lys Lys Tyr Ala Lys Lys Glu Lys Ala Tyr Ala Lys Ala Lys Lys
 1               5                  10                  15

Ala Glu Ala Lys Ala Ala Lys Lys Ala Lys Ala Glu Ala Lys Lys Tyr
             20                  25                  30

Ala Lys Ala Ala Lys Ala Glu Lys Lys Glu Tyr Ala Ala Ala Glu Ala
         35                  40                  45

Lys Tyr Lys Ala Glu Ala Ala Lys Ala Ala Ala Lys Glu Ala Ala Tyr
     50                  55                  60

Glu Ala
 65

<210> SEQ ID NO 5
<211> LENGTH: 77
<212> TYPE: PRT
<213> ORGANISM: Artificial Sequence
<220> FEATURE:
<223> OTHER INFORMATION: Description of Artificial Sequence:   SYNTHETIC
      PEPTIDE

<400> SEQUENCE: 5

Ala Lys Lys Tyr Ala Lys Lys Glu Lys Ala Tyr Ala Lys Lys Ala Glu
 1               5                  10                  15

Lys Ala Ala Lys Lys Ala Glu Ala Lys Ala Tyr Lys Ala Ala Glu Ala
             20                  25                  30

Lys Lys Lys Ala Lys Ala Glu Ala Lys Lys Tyr Ala Lys Ala Ala Lys
         35                  40                  45

Ala Glu Lys Lys Glu Tyr Ala Ala Ala Glu Ala Lys Tyr Lys Ala Glu
     50                  55                  60

Ala Ala Lys Ala Ala Ala Lys Glu Ala Ala Tyr Glu Ala
 65                  70                  75

```
<210> SEQ ID NO 6
<211> LENGTH: 86
<212> TYPE: PRT
<213> ORGANISM: Artificial Sequence
<220> FEATURE:
<223> OTHER INFORMATION: Description of Artificial Sequence:   SYNTHETIC
      PEPTIDE

<400> SEQUENCE: 6

Ala Lys Lys Tyr Ala Lys Lys Glu Lys Ala Tyr Ala Lys Lys Ala Glu
 1               5                  10                  15

Lys Ala Ala Lys Lys Ala Glu Ala Lys Ala Tyr Lys Ala Ala Glu Ala
                20                  25                  30

Lys Lys Lys Ala Lys Ala Glu Ala Lys Lys Tyr Ala Lys Ala Ala Lys
                35                  40                  45

Ala Glu Lys Lys Glu Tyr Ala Ala Ala Glu Ala Lys Tyr Lys Ala Glu
                50                  55                  60

Ala Ala Lys Lys Ala Tyr Lys Ala Glu Ala Ala Lys Ala Ala Ala Lys
65                  70                  75                  80

Glu Ala Ala Tyr Glu Ala
                85

<210> SEQ ID NO 7
<211> LENGTH: 109
<212> TYPE: PRT
<213> ORGANISM: Artificial Sequence
<220> FEATURE:
<223> OTHER INFORMATION: Description of Artificial Sequence:   SYNTHETIC
      PEPTIDE

<400> SEQUENCE: 7

Ala Lys Lys Tyr Ala Lys Lys Ala Glu Lys Ala Tyr Ala Lys Lys Ala
 1               5                  10                  15

Lys Ala Ala Glu Lys Lys Ala Tyr Ala Lys Lys Glu Ala Lys Ala
                20                  25                  30

Tyr Lys Ala Ala Glu Ala Lys Lys Lys Ala Lys Ala Glu Ala Lys Lys
                35                  40                  45

Tyr Ala Lys Glu Ala Ala Lys Ala Lys Lys Glu Ala Tyr Lys Ala Glu
                50                  55                  60

Ala Lys Lys Tyr Ala Lys Ala Ala Lys Ala Glu Lys Lys Glu Tyr Ala
65                  70                  75                  80

Ala Ala Glu Ala Lys Lys Ala Glu Ala Ala Lys Ala Tyr Lys Ala Glu
                85                  90                  95

Ala Ala Lys Ala Ala Ala Lys Glu Ala Ala Tyr Glu Ala
                100                 105
```